United States Patent [19]
Singh et al.

[11] Patent Number: 5,780,646
[45] Date of Patent: *Jul. 14, 1998

[54] CYCLIC ETHER COMPOUNDS

[75] Inventors: Sharat Singh, San Jose; Edwin F. Ullman, Atherton, both of Calif.

[73] Assignee: Behringwerke AG, Marburg, Germany

[*] Notice: The term of this patent shall not extend beyond the expiration date of Pat. No. 5,536,834.

[21] Appl. No.: 660,029

[22] Filed: Jun. 6, 1996

Related U.S. Application Data

[60] Continuation of Ser. No. 471,131, Jun. 6, 1995, Pat. No. 5,536,834, which is a division of Ser. No. 156,181, Nov. 22, 1993, Pat. No. 5,578,498, which is a continuation-in-part of Ser. No. 704,569, May 22, 1991.

[51] Int. Cl.⁶ .................................................. C07D 327/06
[52] U.S. Cl. .................................................................. 549/14
[58] Field of Search ..................................................... 549/14

[56] References Cited

U.S. PATENT DOCUMENTS

| | | |
|---|---|---|
| 3,947,264 | 3/1976 | Graham et al. |
| 4,263,442 | 4/1981 | Puttock. |
| 4,910,303 | 3/1990 | Su et al. |
| 5,536,834 | 7/1996 | Singh et al. .............................. 544/98 |

*Primary Examiner*—Robert W. Ramsuer
*Attorney, Agent, or Firm*—Theodore J. Leitereg

[57] ABSTRACT

Compositions are disclosed comprising (a) a metal chelate wherein the metal is selected from the group consisting of europium, terbium, dysprosium, samarium osmium and ruthenium in at least a hexacoordinated state and (b) a compound having a double bond substituted with two aryl groups, an oxygen atom and an atom selected from the group consisting of oxygen, sulfur and nitrogen wherein one of the aryl groups is electron donating with respect to the other. Such composition is preferably incorporated in a latex particulate material. Methods and kits are also disclosed for determining an analyte in a medium suspected of containing the analyte. The methods and kits employ as one component a composition as described above.

3 Claims, No Drawings

5,780,646

CYCLIC ETHER COMPOUNDS

CROSS-REFERENCE TO RELATED APPLICATIONS

This a continuation of application Ser. No. 08/471,131, filed Jun. 6, 1995, now U.S. Pat. No. 5,536,834, which in turn is a divisional of application Ser. No. 08/156,181, filed Nov. 22, 1993, now U.S. Pat. No. 5,578,498, which in turn is a continuation-in-part of application Ser. No. 07/704,569, filed May 22, 1991, the disclosures of which are incorporated herein.

BACKGROUND OF THE INVENTION

1. Field of the Invention.

This invention relates to methods, compositions and kits for determining an analyte in a sample. In particular, this invention relates to compositions that exhibit a high quantum yield chemiluminescence when activated by singlet oxygen, decay rapidly and emit at long wavelengths.

The clinical diagnostic field has seen a broad expansion in recent years, both as to the variety of materials (analytes) that may be readily and accurately determined, as well as the methods for the determination. Convenient, reliable and non-hazardous means for detecting the presence of low concentrations of materials in liquids is desired. In clinical chemistry these materials may be present in body fluids in concentrations below $10^{-12}$ molar. The difficulty of detecting low concentrations of these materials is enhanced by the relatively small sample sizes that can be utilized.

In developing an assay there are many considerations. One consideration is the signal response to changes in the concentration of analyte. A second consideration is the ease with which the protocol for the assay may be carried out. A third consideration is the variation in interference from sample to sample. Ease of preparation and purification of the reagents, availability of equipment, ease of automation and interaction with material of interest are some of the additional considerations in developing a useful assay.

One broad category of techniques involves the use of a receptor which can specifically bind to a particular spacial and polar organization of a labeled ligand as a function of the presence of an analyte. The observed effect of binding by the receptor will depend upon the label. In some instances the binding of the receptor merely provides for a differentiation in molecular weight between bound and unbound labeled ligand. In other instances the binding of the receptor will facilitate separation of bound labeled ligand from free labeled ligand or it may affect the nature of the signal obtained from the label so that the signal varies with the amount of receptor bound to labeled ligand. A further variation is that the receptor is labeled and the ligand unlabeled. Alternatively, both the receptor and ligand are labeled or different receptors are labeled with two different labels, whereupon the labels interact when in close proximity and the amount of ligand present affects the degree to which the labels of the receptor may interact.

There is a continuing need for new and accurate techniques that can be adapted for a wide spectrum of different ligands or be used in specific cases where other methods may not be readily adaptable.

Homogeneous immunoassays have previously been described for small molecules. These assays include SYVA's FRAT® assay, EMIT® assay, enzyme channeling immunoassay, and fluorescence energy transfer immunoassay (FETI); enzyme inhibitor immunoassays (Hoffman LaRoche and Abbott Laboratories); fluorescence polarization immunoassay (Dandlicker), among others. All of these methods have limited sensitivity, and only a few including FETI and enzyme channeling, are suitable for large multiepitopic analytes. Luminescent compounds, such as fluorescent compounds and chemiluminescent compounds, find wide application in the assay field because of their ability to emit light. For this reason, luminescers have been utilized as labels in assays such as nucleic acid assays and immunoassays. For example, a member of a specific binding pair is conjugated to a luminescer and various protocols are employed. The luminescer conjugate can be partitioned between a solid phase and a liquid phase in relation to the amount of analyte in a sample suspected of containing the analyte. By measuring the luminescence of either of the phases, one can relate the level of luminescence observed to a concentration of the analyte in the sample.

Particles, such as liposomes and erythrocyte ghosts, have been utilized as carriers of encapsulated water soluble materials. For example, liposomes have been employed to encapsulate biologically active material for a variety of uses, such as drug delivery systems wherein a medicament is entrapped during liposome preparation and then administered to the patient to be treated.

Particles, such as latex beads and liposomes, have also been utilized in assays. For example, in homogeneous assays an enzyme may be entrapped in the aqueous phase of a liposome labelled with an antibody or antigen. The liposomes are caused to release the enzyme in the presence of a sample and complement. Antibody—or antigen-labelled liposomes, having water soluble fluorescent or non-fluorescent dyes encapsulated within an aqueous phase or lipid soluble dyes dissolved in the lipid bilayer of the lipid vesicle or in latex beads, have also been utilized to assay for analytes capable of entering into an immunochemical reaction with the surface bound antibody or antigen. Detergents have been used to release the dyes from the aqueous phase of the liposomes.

2. Brief Description of the Related Art.

White, et al. (White), discuss "Chemically Produced Excited States, Energy Transfer, Photochemical Reactions, and Light Emission" in *J. Am. Chem. Soc.*, 93, 6286 (1971).

McCapra, et al. (McCapra), disclose "Metal Catalysed Light Emission from a Dioxetan" in *Tetrahedron Letters*, 23:49, 5225–5228 (1982).

Wildes, et al. (Wildes), discuss "The Dioxetane-Sensitized Chemiluminescence of Lanthanide Chelates. A Chemical Source of 'Monochromatic' Light" in *J. Am. Chem. Soc.*, 93(23), 6286–6288 (1971).

Handley, et al. (Handley), disclose "Effects of Heteroatom Substituents on the Properties of 1,2-Dioxetanes" in *Tetrahedron Letters*, 26, 3183 (1985).

Zaklika, et al. (Zaklika), discuss "Substituent Effects on the Decompositon of 1,2-Dioxetanes" in *J. Am. Chem. Soc.*, 100, 4916 (1978).

European Patent Application No. 0,345,776 (McCapra) discloses specific binding assays that utilize a sensitizer as a label. The sensitizers include any moiety which, when stimulated by excitation with radiation of one or more wavelengths or other chemical or physical stimulus (e.g., electron transfer, electrolysis, electroluminescence or energy transfer) will achieve an excited state which (a) upon interaction with molecular oxygen will produce singlet molecular oxygen, or (b) upon interaction with a leuco dye will assume a reduced form that can be returned to its original unexcited state by interaction with molecular oxygen resulting in the production of hydrogen peroxide. Either interaction with the excited sensitizer will, with the addition of reagents, produce a detectible signal.

European Patent Application No. 0.070,685 (Heller, et al. I) describes a homogeneous nucleic acid hybridization diagnostic by non-radiative energy transfer.

A light-emitting polynucleotide hybridization diagnostic method is described in European Patent Application No. 0.070.687 (Heller, et al. II).

SUMMARY OF THE INVENTION

One aspect of the present invention is directed to compositions comprising (a) a metal chelate comprising a metal selected from the g roup consisting of europium, terbium, dysprosium, samarium, osmium and ruthenium in at least a hexacoordinated state and (b) a compound having a s tructural portion that i s a double bond subst ituted with two aryl groups, an oxygen atom and an atom selected from the group consisting of oxygen, sulfur and nitrogen. The aryl groups are characterized in that one is electron donating with respect to the other. Preferably, the composition i s incorpor ated in a latex particulate material.

Another aspect of the present invention is a compound of the formula:

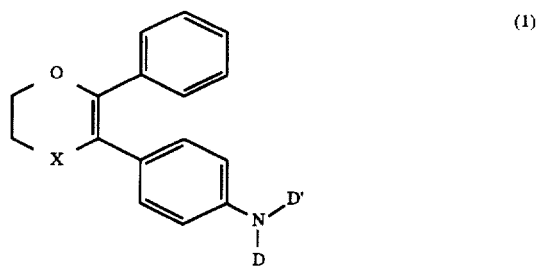

(1)

wherein X' is S or NR' wherein R' is alkyl or aryl and D and D' are independently selected from the group consisting of alkyl and alkyl radical.

Another aspect of the present invention is a composition comprising a latex having incorporated therein a compound of the formula:

(2)

wherein X" is O, S or NR" wherein R" is alkyl or aryl, n is 1 to 4, and Ar and Ar' are independently aryl wherein one of Ar or Ar' is electron donating with respect to the other and Y is hydrogen or an organic radical consisting of atoms selected from the group consisting of C, O, N, S, and P and m is 0 to 2.

Another aspect of the present invention is a composition comprising a latex having incorporated therein Compound 1.

Another aspect of the present invention is a method for determining an analyte which comprises (a) providing in combination (1) a medium suspected of containing an analyte, (2) a photosensitizer capable in its excited state of activating oxygen to a singlet state, where the photosensitizer is associated with a specific binding pair (sbp) member, and (3) one of the above-mentioned compositions incorporated into a latex particulate material having bound thereto an sbp member, (b) treating the combination with light to excite the photosensitizer, and (c) examining the combination for the amount of luminescence emitted therefrom. The amount of luminescence is related to the amount of analyte in the medium.

Another aspect of the present invention is a kit comprising in packaged combination: (1) a composition comprising a suspendible latex particle comprising one of the above-mentioned compounds and (2) a photosensitizer. The particle has bound thereto a specific binding pair (sbp) member. The photosensitizer is capable in its excited state of activating oxygen to its singlet state.

DESCRIPTION OF THE SPECIFIC EMBODIMENTS

The present invention is directed to chemiluminescent compositions that upon activation by singlet oxygen exhibit chemiluminescent emission that rapidly decays, generally having a half life of 0.5 seconds to 30 minutes, preferably 0.5 to 30 seconds, usually less than twenty seconds. In addition, the present chemiluminescent compositions can exhibit high chemiluminescent quantum yield upon activation by singlet oxygen, generally 0.1 to 0.9, usually 0.1 to 0.6, preferably 0.2 to 0.4. The chemiluminescent light emitted by the metal chelate after activation in the present compositions generally has a wave length of about 550 to 700 nm, usually greater than 600 nm. The chemiluminescent compositions of the present invention are particularly useful in luminescent assays. For example, the long wavelength emission avoids interference from serum absorption in assays on blood or serum samples. The high quantum yield improves detectibility and the short lifetime further improves detectibility by causing all the light that is emitted to be delivered in a short pulse rather than over an extended period of time. This can provide higher light intensity at lower quantum yields.

The quantum yield of chemiluminescence of the present chemiluminescent compositions, when activated by singlet oxygen, is generally about 10 to 100 fold greater, preferably, 10 to 50 fold greater, than that observed upon irradiation of the components of the composition separately. Furthermore, the rate of decay of chemiluminescence is significantly enhanced with some of the present compositions. These properties render the present compositions extremely useful in assays for the determination of analytes.

Before proceeding further with a description of the specific embodiments of the present invention, a number of terms will be defined and described in detail.

Metal ligand—a compound in which two or more atoms of the same molecule can coordinate with a metal to form a metal chelate. The metal chelates that form part of the compositions of the present invention comprise a metal selected from the group consisting of europium, terbium, dysprosium, samarium, osmium and ruthenium. One of the above metals is coordinated with one or more metal ligands, which may be, for example, 3-(2-thienoly)-1,1,1-trifluoroacetone (TTA), 3-benzoyl-1,1,1-trifluoroacetone (BFTA), 3-naphthoyl-1,1,1-trifluoroacetone (NPPTA), 2,2-dimethyl-4-perfluorobutyoyl-3-butanone (fod), 2,2'-dipyridyl (bpy), phenanthroline(phen), salicylic acid, phenanthroline carboxylic acid, bipyridyl carboxylic acid, aza crown ethers trioctylphosphine oxide, aza cryptands, and so forth. Usually, the metal in the metal chelate is at least hexacoordinated, but may be octacoordinated or more highly coordinated depending on the metal ligands. The metal chelate will be uncharged, thus the number of acidic groups provided by its ligands will equal the oxidation state of the metal. Usually, the metal ligands will be relatively hydrophobic so as to impart solubility of the metal chelate in non-polar solvents. Rare earth metals will usually have an oxidation state of three, ruthenium will have an oxidation state of two and osmium will have an oxidation state of two. Examplary of such metal chelates, by way of illustration and not limitation, is as follows:

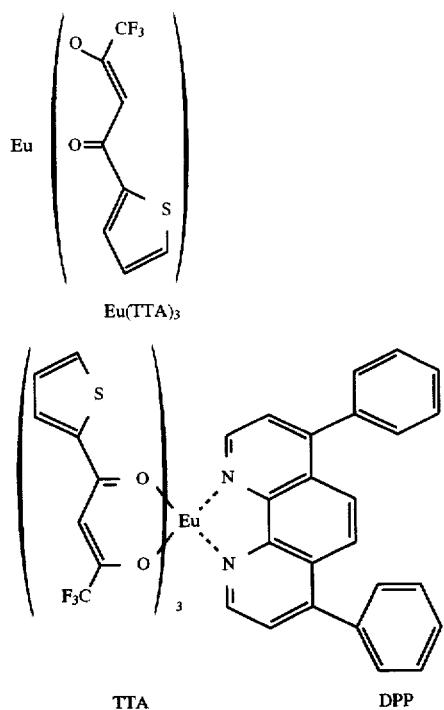

One TTA in 3(a) or 3(b) can be replaced by one of the following:

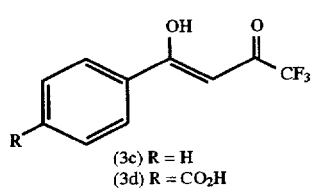

(3c) R = H
(3d) R = CO₂H

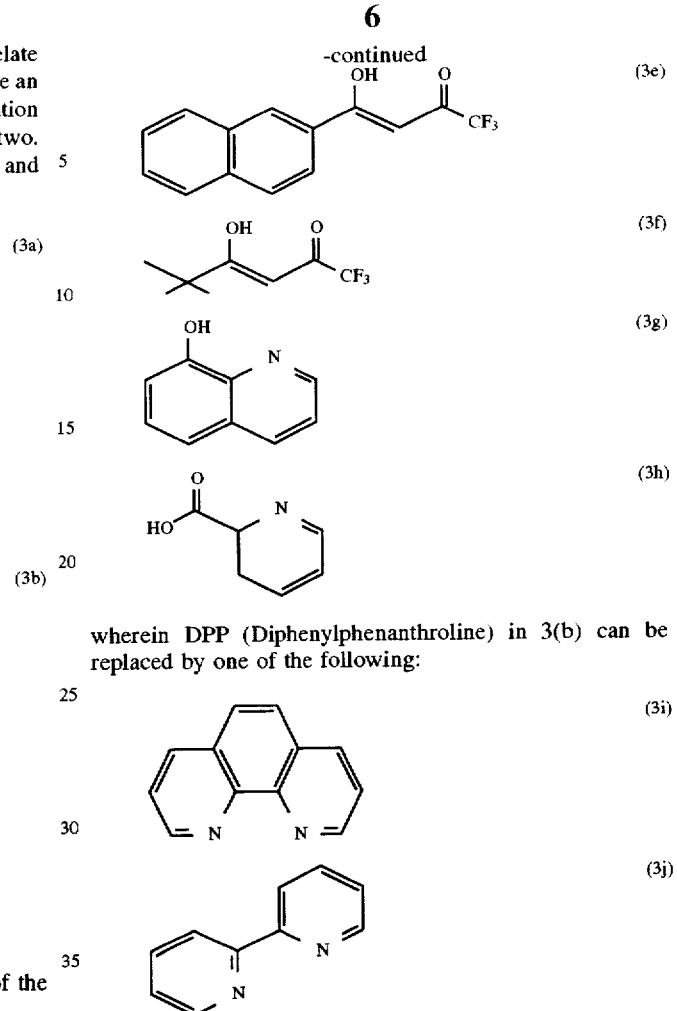

wherein DPP (Diphenylphenanthroline) in 3(b) can be replaced by one of the following:

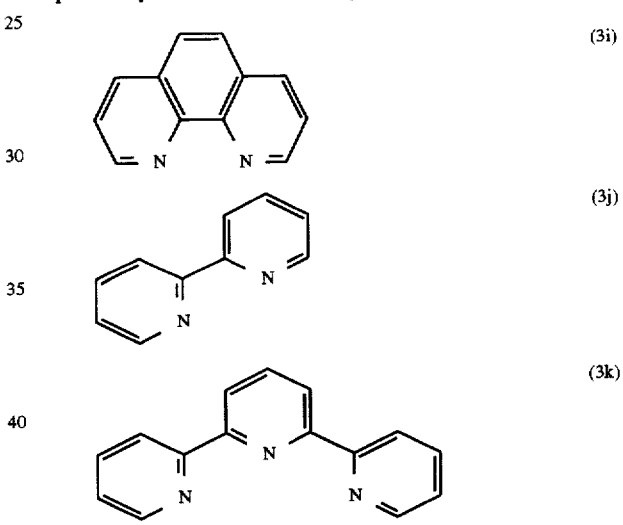

Two TTA's in 3(a) and 3(b) can be independently replaced by compounds selected from the following:

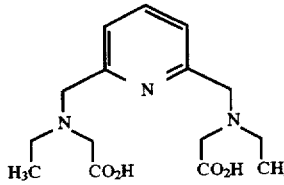

(3l)

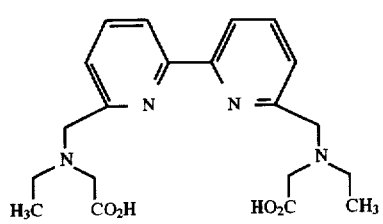

(3m)

-continued
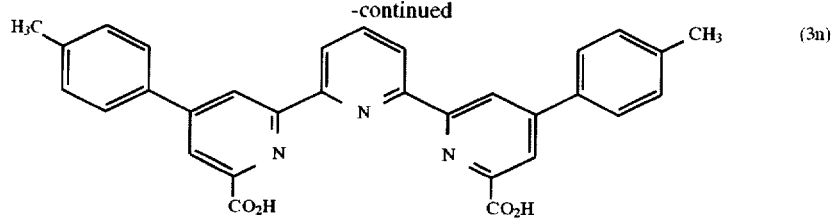
(3n)
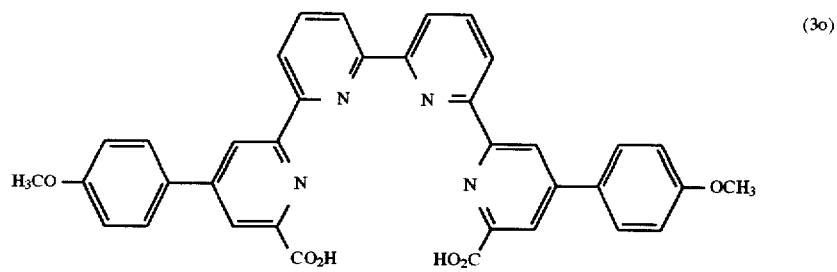
(3o)
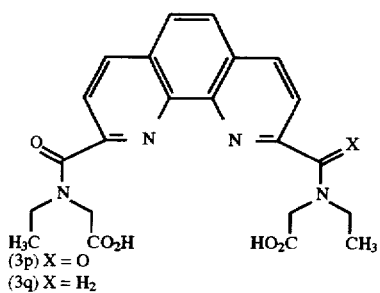
(3p) X = O
(3q) X = H₂
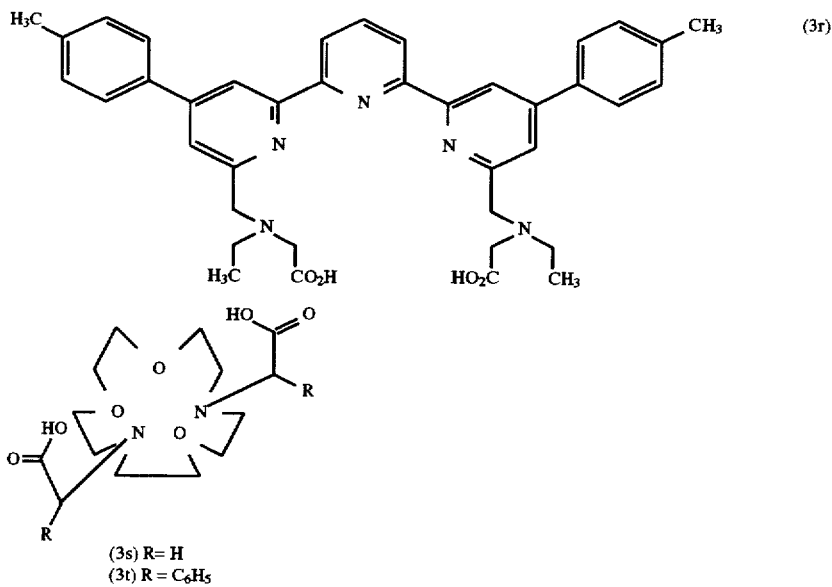
(3r)
(3s) R = H
(3t) R = C₆H₅

Three TTA's can be independently replaced by compounds selected from the following:

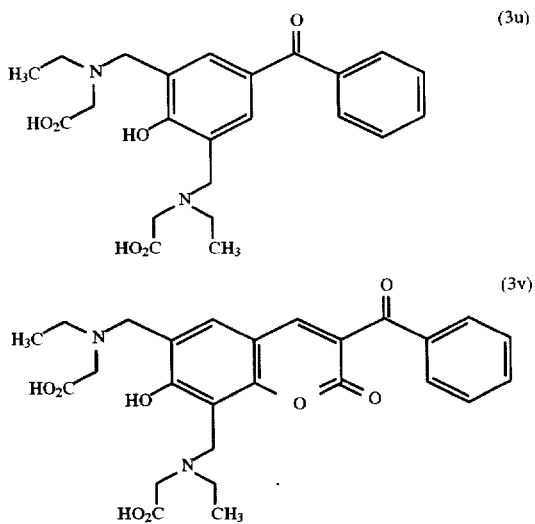

Many of these metal ligands and metal chelates are known in the art and many are commercially available. In general, metal chelates can be prepared from metal ligands by combining the metal chloride with the desired ratio of metal ligand molecules in an organic solvent such as, e.g., acetonitrile and sufficient base, e.g., pyridine, to take up the released hydrochloric acid. For example, metal chelates can be prepared by a procedure such as that described by Shinha, A. P., "Fluorescences and laser action in rare earth chelates," *Spectroscopy Inorganic Chemistry*, Vol 2, (1971), 255–288.

Aryl group—an organic radical derived from an aromatic hydrocarbon by the removal of one atom and containing one or more aromatic rings, usually one to four aromatic rings, which are generally five- or six-member rings such as, e.g., phenyl (from benzene), naphthyl (from naphthalene), biphenylenyl, azulenyl, anthryl, phenanthrenyl, pyridyl, indolyl, benzofuranyl, benzothiophenyl, quinolinyl, isoquinolinyl, carbazolyl, acridinyl, imidazolyl, thiazolyl, pyrazinyl, pyrimidinyl, purinyl, pteridinyl, etc.

Aralkyl—an organic radical having an alkyl group to which is attached an aryl group, e.g., benzyl, phenethyl, 3-phenylpropyl, 1-naphthylethyl, etc.

Electron donating group—a substituent which when bound to a molecule is capable of polarizing the molecule such that the electron donating group becomes electron poor and positively charged relative to another portion of the molecule, i.e., has reduced electron density. Such groups may be, by way of illustration and not limitation, amines, ethers, thioethers, phosphines, hydroxy, oxyanions, mercaptans and their anions, sulfides, etc.

Alkyl—a monovalent branched or unbranched radical derived from an aliphatic hydrocarbon by removal of one H atom; includes both lower alkyl and upper alkyl.

Alkyl radical—a substituent formed from two or more alkyl groups, which may be independently lower or upper alkyl groups, linked together by a functionality such as an ether, including thioether, an amide, an ester and the like.

Lower Alkyl—alkyl containing from 1 to 5 carbon atoms such as, e.g., methyl, ethyl, propyl, butyl, isopropyl, isobutyl, pentyl, isopentyl, etc.

Upper Alkyl—alkyl containing more than 6 carbon atoms, usually 6 to 20 carbon atoms, such as, e.g., hexyl, heptyl, octyl, etc.

Alkylidene—a divalent organic radical derived from an aliphatic hydrocarbon, such as, for example, ethylidene, in which 2 hydrogen atoms are taken from the same carbon atom.

Substituted—means that a hydrogen atom of a molecule has been replaced by another atom, which may be a single atom such as a halogen, etc., or part of a group of atoms forming a functionality such as a substituent having from 1 to 50 atoms (other than the requisite hydrogen atoms necessary to satisfy the valencies of such atoms), which atoms are independently selected from the group consisting of carbon, oxygen, nitrogen, sulfur and phosphorus, and which may or may not be bound to one or more metal atoms.

Analyte—the compound or composition to be detected. The analyte can be comprised of a member of a specific binding pair (sbp) and may be a ligand, which is monovalent (monoepitopic) or polyvalent (polyepitopic), usually antigenic or haptenic, and is a single compound or plurality of compounds which share at least one common epitopic or determinant site. The analyte can be a part of a cell such as bacteria or a cell bearing a blood group antigen such as A, B, D, etc., or an HLA antigen or a microorganism, e.g., bacterium, fungus, protozoan, or virus.

The polyvalent ligand analytes will normally be poly (amino acids), i.e., polypeptides and proteins, polysaccharides, nucleic acids, and combinations thereof. Such combinations include components of bacteria, viruses, chromosomes, genes, mitochondria, nuclei, cell membranes and the like.

For the most part, the polyepitopic ligand analytes to which the subject invention can be applied will have a molecular weight of at least about 5,000, more usually at least about 10,000. In the poly(amino acid) category, the poly(amino acids) of interest will generally be from about 5,000 to 5,000,000 molecular weight, more usually from about 20,000 to 1,000,000 molecular weight; among the hormones of interest, the molecular weights will usually range from about 5,000 to 60,000 molecular weight.

A wide variety of proteins may be considered as to the family of proteins having similar structural features, proteins having particular biological functions, proteins related to specific microorganisms, particularly disease causing microorganisms, etc. Such proteins include, for example, immunoglobulins, cytokines, enzymes, hormones, cancer antigens, nutritional markers, tissue specific antigens, etc.

The following are classes of proteins related by structure: protamines, histones, albumins, globulins, scleroproteins, phosphoproteins, mucoproteins, chromoproteins, lipoproteins, nucleoproteins, glycoproteins, T-cell receptors, proteoglycans, HLA, unclassified proteins, e.g., somatotropin, prolactin, insulin, pepsin, proteins found in the human plasma such as blood clotting factors, other polymeric materials such as mucopolysaccharides and polysaccharides, microorganisms such as bacteria, viruses and fungi.

The monoepitopic ligand analytes will generally be from about 100 to 2,000 molecular weight, more usually from 125 to 1,000 molecular weight. The analytes include drugs, metabolites, pesticides, pollutants, and the like. Included among drugs of interest are the alkaloids, steroids, steroid mimetic substances, lactams, aminoalkylbenzenes, benzheterocyclics, purines, those derived from marijuana, hormones, vitamins, prostaglandins, tricyclic antidepressants, anti-neoplastics, antibiotics, nucleosides and nucleotides, miscellaneous individual drugs which include methadone, meprobamate, serotonin, meperidine, lidocaine, procainamide, acetylprocainamide, propranolol, griseofulvin, valproic acid, butyrophenones, antihistamines, chloramphenicol, anticholinergic drugs, such as atropine, metabolites related to diseased states include spermine, galactose, phenylpyruvic acid, and porphyrin Type 1, aminoglycosides, polyhalogenated biphenyls, phosphate esters, thiophosphates, carbamates, polyhalogenated sulfenamides.

For receptor analytes, the molecular weights will generally range from 10,000 to $2\times10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally-being at least about 25,000 molecular weight and may be $10^6$ or higher molecular weight, including such materials as avidin, DNA, RNA, thyroxine binding globulin, thyroxine binding prealbumin, transcortin, etc.

The term analyte further includes polynucleotide analytes such as those polynucleotides defined below. These include m-RNA, r-RNA, t-RNA, DNA, DNA-RNA duplexes, etc. The term analyte also includes receptors that are polynucleotide binding agents, such as, for example, restriction enzymes, activators, repressors, nucleases, polymerases, histones, repair enzymes, chemotherapeutic agents, and the like.

The analyte may be a molecule found directly in a sample such as a body fluid from a host. The sample can be examined directly or may be pretreated to render the analyte more readily detectible. Furthermore, the analyte of interest may be determined by detecting an agent probative of the analyte of interest such as a specific binding pair member complementary to the analyte of interest, whose presence will be detected only when the analyte of interest is present in a sample. Thus, the agent probative of the analyte becomes the analyte that is detected in an assay. The body fluid can be, for example, urine, blood, plasma, serum, saliva, semen, stool, sputum, cerebral spinal fluid, tears, mucus, and the like.

Member of a Specific Binding Pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These will usually be members of an immunological pair such as antigen-antibody, although other specific binding pairs such as biotin-avidin, hormones-hormone receptors, nucleic acid duplexes, IgG-protein A, polynucleotide pairs such as DNA-DNA, DNA-RNA, and the like are not immunological pairs but are included in the invention and the definition of sbp member.

Polynucleotide—a compound or composition which is a polymeric nucleotide having in the natural state about 50 to 500,000 or more nucleotides and having in the isolated state about 15 to 50,000 or more nucleotides, usually about 15 to 20,000 nucleotides, more frequently 15 to 10,000 nucleotides. The polynucleotide includes nucleic acids from any source in purified or unpurified form, naturally occurring or synthetically produced, including DNA (dsDNA and ssDNA) and RNA, usually DNA, and may be t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like.

Ligand—any organic compound for which a receptor naturally exists or can be prepared.

Ligand Analog—a modified ligand, an organic radical or analyte analog, usually of a molecular weight greater than 100, which can compete with the analogous ligand for a receptor, the modification providing means to join a ligand analog to another molecule. The ligand analog will usually differ from the ligand by more than replacement of a hydrogen with a bond which links the ligand analog to a hub or label, but need not. The ligand analog can bind to the receptor in a manner similar to the ligand. The analog could be, for example, an antibody directed against the idiotype of an antibody to the ligand.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, protein A, complement component C1q, and the like.

Specific binding—the specific recognition of one of two different molecules for the other compared to substantially less recognition of other molecules. Generally, the molecules have areas on their surfaces or in cavities giving rise to specific recognition between the two molecules. Exemplary of specific binding are antibody-antigen interactions, enzyme-substrate interactions, polynucleotide interactions, and so forth.

Non-specific binding—non-covalent binding between molecules that is relatively independent of specific surface structures. Non-specific binding may result from several factors including hydrophobic interactions between molecules.

Antibody—an immunoglobulin which specifically binds to and is thereby defined as complementary with a particular spatial and polar organization of another molecule. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, etc. Fragments thereof may include Fab, Fv and F(ab')$_2$, Fab', and the like. In addition, aggregates, polymers, and conjugates of immunoglobulins or their fragments can be used where appropriate so long as binding affinity for a particular molecule is maintained.

A substituent having from 1 to 50 atoms (other than the requisite hydrogen atoms necessary to satisfy the valencies of such atoms), which atoms are independently selected from the group consisting of carbon, oxygen, nitrogen, sulfur and phosphorus—an organic radical; the organic radical has 1 to 50 atoms other than the requisite number of hydrogen atoms necessary to satisfy the valencies of the atoms in the radical. Generally, the predominant atom is carbon (C) but may also be oxygen (O), nitrogen (N), sulfur (S), phosphorus (P), wherein the O, N, S, or P, if present, are bound to carbon or one or more of each other or to hydrogen or a metal atom to form various functional groups, such as, for example, carboxylic acids, alcohols, thiols, carboxamides, carbamates, carboxylic acid esters, sulfonic acids, sulfonic acid esters, phosphoric acids, phosphoric acid esters, ureas, carbamates, phosphoramides, sulfonamides, ethers, sulfides, thioethers, olefins, acetylenes, amines, ketones, aldehydes, nitrites, and the like. Illustrative of such organic radicals or groups, by way of illustration and not limitation, are alkyl, alkylidine, aryl, aralkyl, and alkyl, aryl, and aralkyl substituted with one or more of the aforementioned functionalities.

Linking group—the covalent linkage between molecules. The linking group will vary depending upon the nature of the molecules, i.e., photosensitizer, chemiluminescent compound, sbp member or molecule associated with or part of a particle, being linked. Functional groups that are normally present or are introduced on a photosensitizer or chemiluminescent compound will be employed for linking these materials to an sbp member or a particle such as a latex particle.

For the most part, carbonyl functionalities will find use, both oxocarbonyl, e.g., aldehyde and non-oxocarbonyl (including nitrogen and sulfur analogs) e.g., carboxy, amidine, amidate, thiocarboxy and thionocarboxy.

Alternative functionalities of oxo include active halogen, diazo, mercapto, olefin, particularly activated olefin, amino, phosphoro and the like. A description of linking groups may be found in U.S. Pat. No. 3,817,837, which disclosure is incorporated herein by reference.

Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, the photosensitizer and chemilumenescent compound will have a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α, β-unsaturated ester. These functionalities will be linked to amine groups, carboxyl groups, active olefins, alkylating agents, e.g., bromoacetyl. Where an amine and carboxylic acid or its nitrogen derivative or phophoric acid are linked, amides, amidines and phosphoramides will be formed. Where mercaptan and activated olefin are linked, thioethers will be formed. Where a mercaptan and an alkylating agent are linked, thioethers will be formed. Where aldehyde and an amine are linked under reducing conditions, an alkylamine will be formed. Where a carboxylic acid or phosphate acid and an alcohol are linked, esters will be formed.

Photosensitizer—a sensitizer for generation of singlet oxygen usually by excitation with light. The photosensitizer can be photoactivatable (e.g., dyes and aromatic compounds) or chemiactivated (e.g., enzymes and metal salts). When excited by light the photosensitizer is usually a compound comprised of covalently bonded atoms, usually with multiple conjugated double or triple bonds. The compound should absorb light in the wavelength range of 200–1100 nm, usually 300–1000 nm, preferably 450–950 nm, with an extinction coefficient at its absorbance maximum greater than $500M^{-1}cm^{-1}$, preferably at least $5000M^{-1}cm^{-1}$, more preferably at least $50,000M^{-1}cm^{-1}$ at the excitation wavelength. The lifetime of an excited state produced following absorption of light in the absence of oxygen will usually be at least 100 nsec, preferably at least 1 msec. In general, the lifetime must be sufficiently long to permit energy transfer to oxygen, which will normally be present at concentrations in the range of $10^{-5}$ to $10^{-3}M$ depending on the medium. The sensitizer excited state will usually have a different spin quantum number (S) than its ground state and will usually be a triplet (S=1) when, as is usually the case, the ground state is a singlet (S=0). Preferably, the sensitizer will have a high intersystem crossing yield. That is, photoexcitation of a sensitizer will produce the long lived state (usually triplet) with an efficiency of at least 10%, desirably at least 40%, preferably greater than 80%. The photosensitizer will usually be at most weakly fluorescent under the assay conditions (quantum yield usually less that 0.5, preferably less that 0.1).

Photosensitizers that are to be excited by light will be relatively photostable and will not react efficiently with singlet oxygen. Several structural features are present in most useful sensitizers. Most sensitizers have at least one and frequently three or more conjugated double or triple bonds held in a rigid, frequently aromatic structure. They will frequently contain at least one group that accelerates intersystem crossing such as a carbonyl or imine group or a heavy atom selected from rows 3–6 of the periodic table, especially iodine or bromine, or they may have extended aromatic structures. Typical sensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives of these compounds having substituents of 1 to 50 atoms for rendering such compounds more lipophilic or more hydrophilic and/or as attaching groups for attachment, for example, to an sbp member. Examples of other photosensitizers that may be utilized in the present invention are those that have the above properties and are enumerated in N.J. Turro, "Molecular Photochemistry", page 132, W. A. Benjamin Inc., N.Y. 1965.

The photosensitizers are preferably relatively non-polar to assure dissolution into a lipophilic member when the photosensitizer is incorporated in an oil droplet, liposome, latex particle, etc.

The photosensitizers useful in this invention are also intended to include other substances and compositions that can produce singlet oxygen with or, less preferably, without activation by an external light source. Thus, for example, molybdate ($MoO_4^=$) salts and chloroperoxidase and myeloperoxidase plus bromide or chloride ion (Kanofsky, J. Biol. Chem. (1983) 259 5596) have been shown to catalyze the conversion of hydrogen peroxide to singlet oxygen and water. Either of these compositions can, for example, be included in particles to which is bound an sbp member and used in the assay method wherein hydrogen peroxide is included as an ancillary reagent, chloroperoxidase is bound to a surface and molybdate is incorporated in the aqueous phase of a liposome. Also included within the scope of the invention as photosensitizers are compounds that are not true sensitizers but which on excitation by heat, light, or chemical activation will release a molecule of singlet oxygen. The best known members of this class of compounds includes the endoperoxides such as 1,4-biscarboxyethyl-1,4-naphthalene endoperoxide, 9,10-diphenylanthracene-9,10-endoperoxide and 5,6,11,12-tetraphenyl naphthalene 5,12-endoperoxide. Heating or direct absorption of light by these compounds releases singlet oxygen.

Support or Surface—a surface comprised of a porous or non-porous water insoluble material. The surface can have any one of a number of shapes, such as strip, rod, particle, including bead, and the like. The surface can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970).

Particles—particles of at least about 20 nm and not more than about 20 microns, usually at least about 40 nm and less than about 10 microns, preferably from about 0.10 to 2.0 microns diameter, normally having a volume of less than 1 picoliter. The particle may be organic or inorganic, swellable or non-swellable, porous or non-porous, having any density, but preferably of a density approximating water, generally from about 0.7 to about 1.5 g/ml, preferably suspendible in water, and composed of material that can be transparent, partially transparent, or opaque. The particles may or may not have a charge, and when they are charged, they are preferably negative. The particles may be solid (e.g., polymer, metal, glass, organic and inorganic such as minerals, salts and diatoms), oil droplets (e.g., hydrocarbon, fluorocarbon, silicon fluid), or vesicles (e.g., synthetic such as phospholipid or natural such as cells and organelles). The particles may be latex particles or other particles comprised of organic or inorganic polymers; lipid bilayers, e.g., liposomes, phospholipid vesicles; oil droplets; silicon particles; metal sols; cells; and dye crystallites.

The organic particles will normally be polymers, either addition or condensation polymers, which are readily dispersible in the assay medium. The organic particles will also be adsorptive or functionalizable so as to bind at their surface, either directly or indirectly, an sbp member and to bind at their surface or incorporate within their volume a photosensitizer or a chemiluminescent compound.

The particles can be derived from naturally occurring materials, naturally occurring materials which are synthetically modified and synthetic materials. Natural or synthetic assemblies such as lipid bilayers, e.g., liposomes and non-phospholipid vesicles, are preferred. Among organic polymers of particular interest are polysaccharides, particularly cross-linked polysaccharides, such as agarose, which is available as Sepharose, dextran, available as Sephadex and Sephacryl, cellulose, starch, and the like; addition polymers, such as polystyrene, polyacrylamide, homopolymers and copolymers of derivatives of acrylate and methacrylate, particularly esters and amides having free hydroxyl functionalities including hydrogels, and the like. Inorganic polymers include silicones, glasses, available as Bioglas, and the like. Sols include gold, selenium, and other metals. Particles may also be dispersed water insoluble dyes such as porphyrins, phthalocyanines, etc., which may also act as photosensitizers. Particles may also include diatoms, cells, viral particles, magnetosomes, cell nuclei and the like.

Where the particles are commercially available, the particle size may be varied by breaking larger particles into smaller particles by mechanical means, such as grinding, sonication, agitation, etc.

The particles will usually be polyfunctional or be capable of being polyfunctionalized or be capable of being bound to an sbp member, photosensitizer, or chemiluminescent compound through specific or non-specific covalent or non-covalent interactions. A wide variety of functional groups are available or can be incorporated. Exemplary functional groups include carboxylic acids, aldehydes, amino groups, cyano groups, ethylene groups, hydroxyl groups, mercapto groups and the like. When covalent attachment of a sbp member, chemiluminescent compound or photosensitizer to the particle is employed, the manner of linking is well known and is amply illustrated in the literature. See for example Cautrecasas, *J. Biol. Chem.*, 245:3059 (1970). The length of a linking group may vary widely, depending upon the nature of the compound being linked, the nature of the particle, the effect of the distance between the compound being linked and the particle on the binding of sbp members and the analyte and the like.

The photosensitizer can be chosen to dissolve in or noncovalently bind to the surface of the particles. In this case these compounds will preferably be hydrophobic to reduce their ability to dissociate from the particle and thereby cause both compounds to associate with the same particle.

The number of photosensitizer or chemiluminescent molecules associated with each particle will on the average usually be at least one and may be sufficiently high that the particle consists entirely of photosensitizer or chemiluminescer molecules. The preferred number of molecules will be selected empirically to provide the highest signal to background in the assay. In some cases this will be best achieved by associating a multiplicity of different photosensitizer molecules to particles. Usually, the photosensitizer or chemiluminescent compound to sbp member ratio in the particles should be at least 1, preferably at least 100 to 1, and most preferably over 1,000 to 1.

Latex particles—"Latex" signifies a particulate water suspendible water insoluble polymeric material usually having particle dimensions of 20 nm to 20 mm, more preferably 100 to 1000 nm in diameter. The latex is frequently a substituted polyethylene such as: polystyrene-butadiene, polyacrylamide polystyrene, polystyrene with amino groups, poly-acrylic acid, polymethacrylic acid, acrylonitrile-butadiene, styrene copolymers, polyvinyl acetate-acrylate, polyvinyl pyrridine, vinyl-chloride acrylate copolymers, and the like. Non-crosslinked polymers of styrene and carboxylated styrene or styrene functionalized with other active groups such as amino, hydroxyl, halo and the like are preferred. Frequently, copolymers of substituted styrenes with dienes such as butadiene will be used.

The association of the photosensitizer or chemiluminescent compound with latex particles utilized in the present invention may involve incorporation during formation of the particles by polymerization but will usually involve incorporation into preformed particles, usually by noncovalent dissolution into the particles. Usually a solution of the chemiluminescent compound or sensitizer will be employed. Solvents that may be utilized include alcohols, including ethanol, ethylene glycol and benzyl alcohol; amides such as dimethyl formamide, formamide, acetamide and tetramethyl urea and the like; sulfoxides such as dimethyl sulfoxide and sulfolane; and ethers such as carbitol, ethyl carbitol, dimethoxy ethane and the like, and water. The use of solvents having high boiling points in which the particles are insoluble permits the use of elevated temperatures to facilitate dissolution of the compounds into the particles and are particularly suitable. The solvents may be used singly or in combination. Particularly preferred solvents for incorporating photosensitizer are those that will not quench the triplet excited state of the photosensitizer either because of their intrinsic properties or because they can subsequently be removed from the particles by virtue of their ability to be dissolved in a solvent such as water that is insoluble in the particles. Aromatic solvents are preferred, and generally solvents that are soluble in the particle. For incorporating chemiluminescent compounds in particles a solvent should be selected that does not interfere with the luminescence because of their intrinsic properties or ability to be removed from the particles. Frequently, aromatic solvents will also be preferred. Typical aromatic solvents include dibutylphthalate, benzonitrile, naphthonitrile, dioctylterephthalate, dichlorobenzene, diphenylether, dimethoxybenzene, etc.

Except when the photosensitizer or chemiluminescent compound is to be covalently bound to the particles, it will usually be preferable to use electronically neutral photosensitizers or chemiluminescent compounds. It is preferable that the liquid medium selected does not soften the polymer beads to the point of stickiness. A preferred technique comprises suspending the selected latex particles in a liquid medium in which the photosensitizer or chemiluminescent compound has at least limited solubility. Preferably, the concentrations of the photosensitizer and chemiluminescent compound in the liquid media will be selected to provide particles that have the highest efficiency of singlet oxygen formation and highest quantum yield of emission from the chemiluminescent compound in the media but less concentrated solutions will sometimes be preferred. Distortion or dissolution of the particles in the solvent can be prevented by adding a miscible cosolvent in which the particles are insoluble.

Generally, the temperature employed during the procedure will be chosen to maximize the singlet oxygen formation ability of the photosensitizer labeled particles and the quantum yield of the chemiluminescent compound particles with the proviso that the particles should not melt or become aggregated at the selected temperature. Elevated temperatures are normally employed. The temperatures for the procedure will generally range from 20° C. to 200° C., more usually from 50° C. to 170° C. It has been observed that some compounds that are nearly insoluble at room temperature, are soluble in, for example, low molecular weight alcohols, such as ethanol and ethylene glycol and the like, at elevated temperatures. Carboxylated modified latex particles have been shown to tolerate low molecular weight alcohols at such temperatures.

An sbp member may be physically adsorbed on the surface of the latex particle or may be covalently bonded to the particle. In cases wherein the sbp member is only weakly bound to the surface of the latex particle, the binding may in certain cases be unable to endure particle-to-particle shear forces encountered during incubation and washings. Therefore, it may be preferable to covalently bond sbp members to the latex particles under conditions that will minimize adsorption. This may be accomplished by chemically activating the surface of the latex. For example, the N-hydroxysuccinimide ester of surface carboxyl groups can be formed and the activated particles to reduce nonspecific binding of assay components to the particle surface, are then contacted with a linker having amino groups that will react with the ester groups or directly with an sbp member that has an amino group. The linker will usually be selected to reduce nonspecific binding of assay components to the particle surface and will preferably provide suitable functionality for both attachment to the latex particle and attachment of the sbp member. Suitable materials include maleimidated aminodextran (MAD), polylysine, aminosaccharides, and the like. MAD can be prepared as described by Hubert, et al., *Proc. Natl. Acad. Sci.*, 75(7), 3143, 1978.

In one method, MAD is first attached to carboxyl-containing latex particles using a water soluble carbodiimide, for example, 1-(3-dimethylaminopropyl)-3-ethyl carbodiimide. The coated particles are then equilibrated in reagents to prevent nonspecific binding. Such reagents include proteins such as bovine gamma globulin (BGG), and detergent, such as Tween 20, TRITON X-100 and the like. A sbp member having a sulfhydryl group, or suitably modified to introduce a sulfhydryl group, is then added to a suspension of the particles, whereupon a covalent bond is formed between the sbp member and the MAD on the particles. Any excess unreacted sbp member can then be removed by washing.

Chemiluminescent compound—compounds that form part of the compositions of the present invention are enol ethers generally having the structural portion selected from the group consisting of:

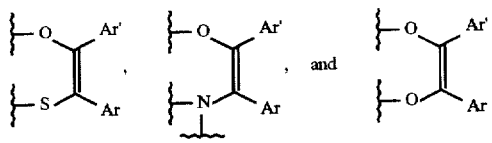

wherein Ar and Ar' are independently aryl wherein one of Ar or Ar', preferably Ar, is electron donating with respect to the other. This may be achieved, for example, by the presence of one or more electron donating groups in one of Ar or Ar'. The part of the above structures represented by the broken lines are not critical to the present invention and may be any substituent as long as such substituent does not interfere with dioxetane formation and transfer of energy. Generally, the compounds are those of Compound 2 wherein, preferably, m is 0, and n is 1 to 3.

For the most part the compounds that form part of the present composition have the structural portion:

(7)

wherein X is O, S or N wherein the valency of N is completed with hydrogen or an organic radical consisting of atoms selected from the group consisting of C, O, N, S, and P and Ar and Ar' are independently aryl wherein one of Ar or Ar' is electron donating with respect to the other.

The broken lines in the above structure signify that the ring can be independently unsubstituted or substituted with a substituent having from 1 to 50 atoms. In addition, the substituents may be taken together to form a ring such as, for example, aryl, which may in turn be substituted with a substituent having from 1 to 50 atoms.

Exemplary enol ethers, by way of illustration and not limitation, are set forth in the following chart with reference to the following structure:

(8)

wherein Compounds 9–17 have the following moieties for X, Ar, and Ar'.

| X | Ar | Ar' | * |
|---|----|-----|---|
| O | 4-N(CH$_3$)$_2$-C$_6$H$_4$- | C$_6$H$_5$- | 9 |
| S | C$_6$H$_5$- | 4-N(CH$_3$)$_2$-C$_6$H$_4$- | 10 |
| S | 4-N(CH$_3$)$_2$-C$_6$H$_4$- | C$_6$H$_5$- | 11 |
| S | C$_6$H$_5$- | C$_6$H$_5$- | 12 |
| S | 4-[-NCH$_2$(CH$_2$)$_3$CH$_2$C(=O)-, [CH$_3$(CH$_2$)$_9$]$_2$-N]-C$_6$H$_4$- | C$_6$H$_5$- | 13 |
| S | 4-N[(CH$_2$)$_9$CH$_3$]$_2$-C$_6$H$_4$- | 4-(CH$_2$)$_6$CH$_3$-C$_6$H$_4$- | 14 |
| S | 4-N(CH$_3$)$_2$-C$_6$H$_4$- | 4-(CH$_2$)$_7$CH$_3$-C$_6$H$_4$- | 15 |
| 2-pyridyl | 4-N(CH$_3$)$_2$-C$_6$H$_4$- | C$_6$H$_5$- | 16 |
| C$_6$H$_5$- | 1-methyl-indol-3-yl 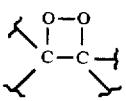 | C$_6$H$_5$- | 17 |

*Compounds 9–17

The chemiluminescent compounds undergo a chemical reaction with singlet oxygen to form a metastable intermediate that can decompose with the simultaneous or subsequent emission of light within the wavelength range of 250 to 1200 nm. Preferably, the intermediate decomposes spontaneously without heating or addition of ancillary reagents following its formation. However, addition of a reagent after formation of the intermediate or the use of elevated temperature to accelerate decomposition will be required for some chemiluminescent compounds. The chemiluminescent compounds are usually electron rich compounds that react with singlet oxygen, frequently with formation of dioxetanes or dioxetanones, such as those represented by the following structure where the substituents on the carbon (C) atoms are those present on the corresponding olefin:

$$\begin{array}{c} \diagdown \phantom{xx} O-O \phantom{xx} \diagup \\ \phantom{xxx} C-C \\ \diagup \phantom{xxxxxxx} \diagdown \end{array}$$

some of which decompose spontaneously, others by heating and/or by catalysis usually by an electron rich energy acceptor, with the emission of light. For some cases the dioxetane is spontaneously converted to a hydroperoxide whereupon basic pH is required to reform the dioxetane and permit decomposition and light emission.

The chemiluminescent compounds of interest will generally emit at wavelengths above 300 nanometers and usually above 400 nm. Compounds that alone or together with a fluorescent molecule emit light at wavelengths beyond the region where serum components absorb light will be of particular use in the present invention. The fluorescence of serum drops off rapidly above 500 nm and becomes relatively unimportant above 550 nm. Therefore, when the analyte is in serum, chemiluminescent compounds that emit light above 550 nm, preferably above 600 nm are of particular interest. In order to avoid autosensitization of the chemiluminescent compound, it is preferable that the chemiluminescent compounds do not absorb light used to excite the photosensitizer. Since it will generally be preferable to excite the sensitizer with light wavelengths longer than 500 nm, it will therefore be desirable that light absorption by the chemiluminescent compound be very low above 500nm.

The chemiluminescent compounds of the present invention can be prepared in a number of different ways. In one approach a 2-thioethanol derivative is condensed with an appropriate diaryl substituted alpha-hydroxy ketone (substituted benzoin) where one aryl is substituted on the ketone carbon and the other is substituted on the carbon containing the alpha-hydroxy group. The condensation reaction yields the appropriate enol ether directly. The above condensation can be carried out in an inert solvent such as toluene. Usually, the temperature of the reaction is about 90°–130° and the reaction is allowed to proceed for a period of 5–50 hours. Generally, the reaction is carried out at the reflux temperature of the combined reagents. The condensation is carried out in the presence of a Lewis acid, for example, an acyl chloride, silyl chloride, stannous chloride, etc. The following reaction scheme is illustrative of the above-described method for preparing the chemiluminescent compounds of the present invention:

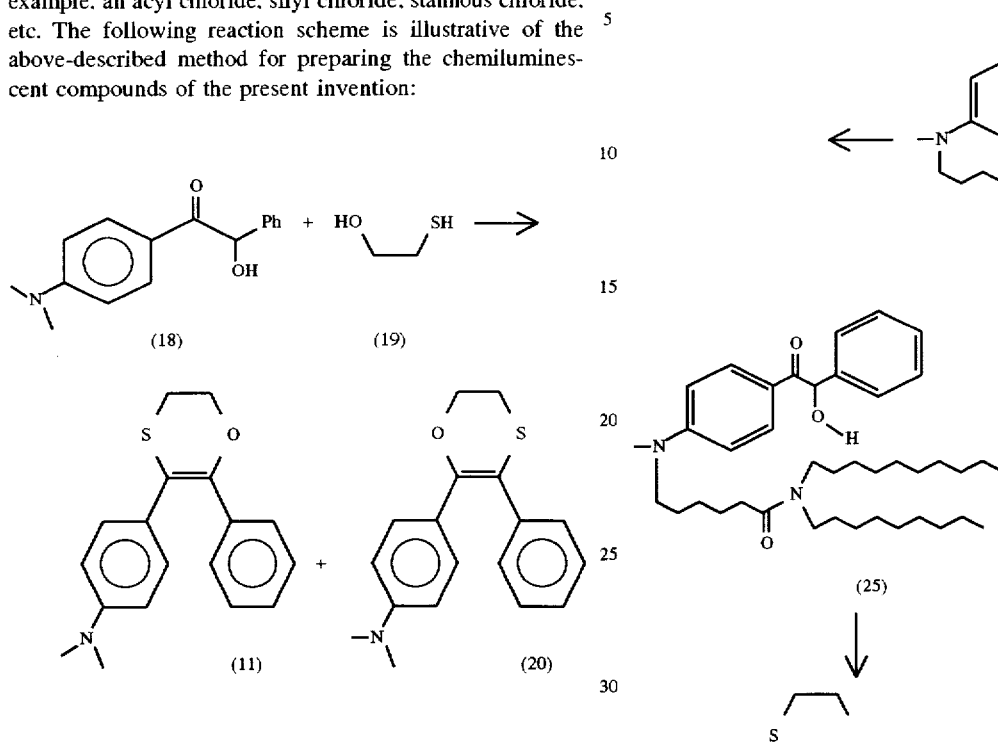

Another reaction scheme for preparing compounds in accordance with the present invention, particularly those containing an alkyl radical, is depicted in the following schematic for synthesizing Compound 13:

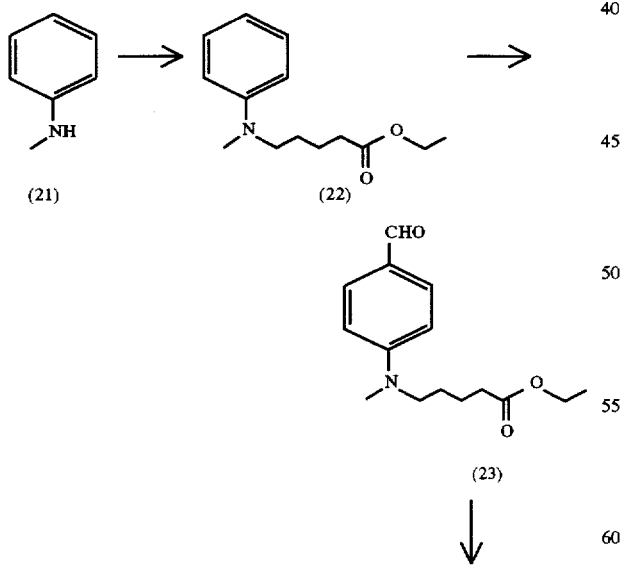

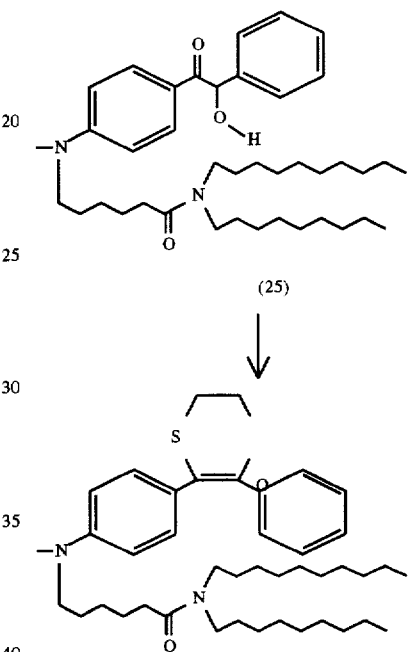

In the above synthesis ethyl 5-bromovalerate is condensed with N-methylaniline to give 22 which is converted by Kilsmeier-Haak synthesis (DMF/POCl₃) to aldehyde 23. Benzoin condensation of 23 with benzaldehyde yields 24 which is hydrolyzed with potassium hydroxide and converted to amide 25 with didecylamine and diphenylphosphoryl azide (DPPA). Conversion to Compound 13 was carried out by condensation with mercaptoethanol and trimethylsilylchloride.

Another approach for preparing compounds in accordance with the present invention, particularly involving regioselective synthesis is shown in the following schematic for synthesizing Compound 14:

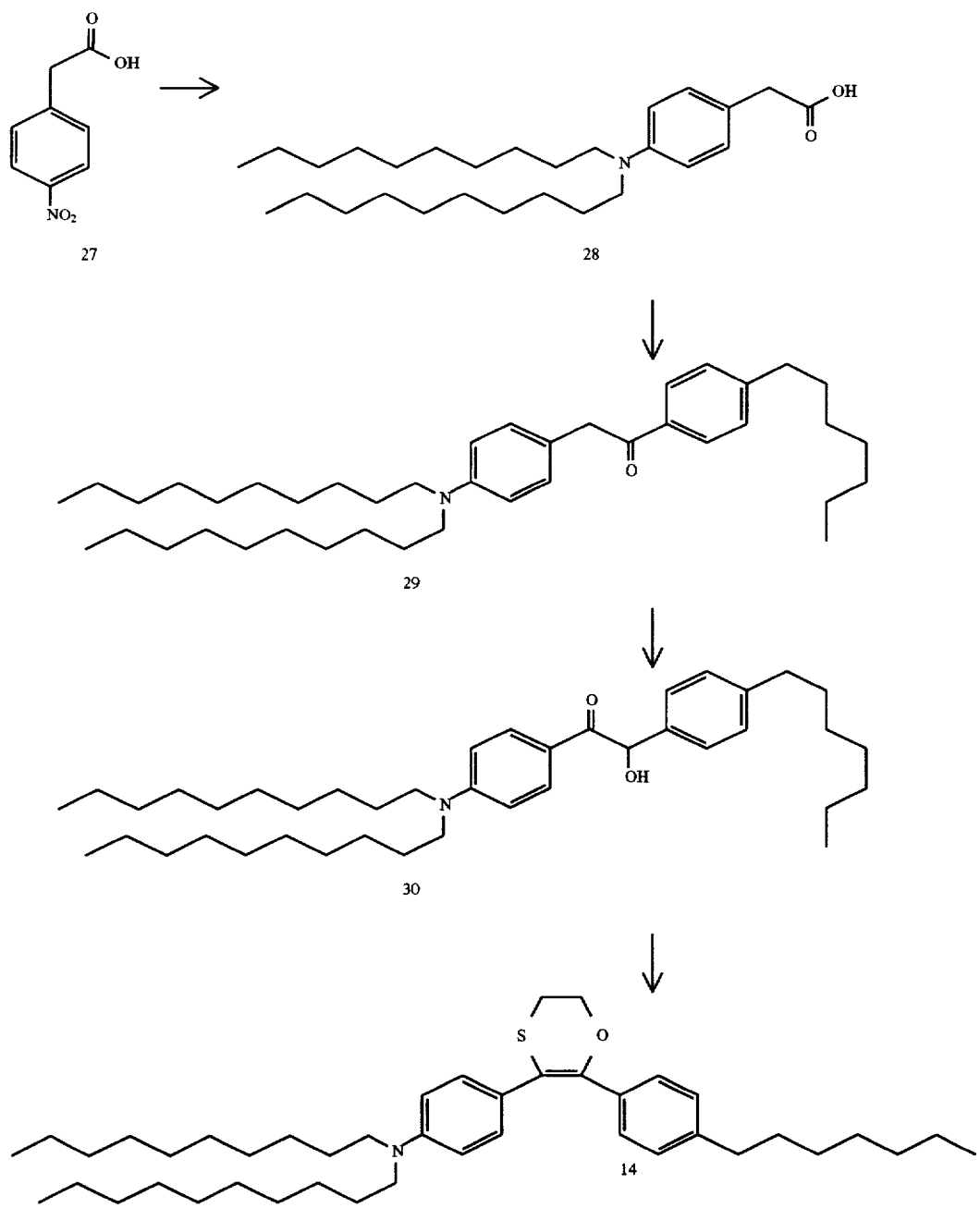

In the above synthesis reaction of p-nitrophenylacetic acid (27) with decanal in the presence of pd/carbon and hydrogen gas at 100 psi gives didecylamine 28, which is condensed with p-heptylbenzene to give ketone 29. Bromine and trifluoroacetic acid are used to brominate 29 and bicarbonate converts the product to benzoin 30. Conversion to Compound 14 is carried out by condensation with mercaptoethanol and trimethylsilylchloride.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like. When the photosensitizer is activated chemically rather than by irradiation, hydrogen peroxide will often be included as an ancillary reagent. When it is desired to shift the emission wavelength of the chemiluminescent compound to longer wavelength or catalyse the decomposition of its oxygen-activated form, a fluorescent molecule may be employed.

Wholly or Partially Sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

One aspect of the present invention is directed to compositions comprising (a) a metal chelate comprising a metal selected from the group consisting of europium, terbium, dysprosium, samarium, osmium and ruthenium in at least a hexacoordinated state and (b) a compound having a structural portion that is a double bond substituted with two aryl groups, an oxygen atom and an atom selected from the group consisting of oxygen, sulfur and nitrogen. The aryl groups are characterized in that one is electron donating with respect to the other. The composition of the present invention comprising a metal chelate and an olefinic compound is generally in a medium that may be liquid or solid, usually solid particulate. The liquid medium is usually a high-boiling, water immisinble liquid such as one from the group comprising toluene, lipids, fluorocarbons, diphenylether, chlorobenzene, dioctylphthalate, dimethoxybenzene, mineral oil and triacylglycerides and the solid particulate medium can be an organic polymer such as polystyrene, polymethylacrylate, polyacrylate, polyacrylamide, polyvinylchloride and copolymers thereof, nylon and other polyamides, etc. Preferably, the composition is incorporated in a latex particulate material.

The metal chelate is present in an amount to maximize the chemiluminescent quantum yield and minimize the decay time of chemiluminescence. Usually, the metal chelate is present at 0.2–500 mM, preferably 2–100 mM. In some circumstances, usually when the metal chelate is hexacoordinated, reduction in the decay time is accompanied by a reduction in quantum yield and a balance must be reached between these two effects. Accordingly, the concentration of the metal chelate in the composition should be adjusted to achieve such a balance. The concentration of the chemiluminescent compound in the composition is usually 0.1–500 mM, preferably 2–100 mM.

Preferred compounds of the present invention have the formula of Compound 1. Representative of such compounds are Compounds 10–16. Particularly preferred compounds are those of the formula of Compound 1 wherein X' is S or NR' wherein R' is lower alkyl or aryl and D and D' are independently lower alkyl, preferably wherein X' is S. Particularly preferred compounds within the above are those wherein D and D' are methyl and R' is methyl or phenyl, and a most preferred compound is one in which X' is S and D and D' are methyl. Compound 13 is one of the more preferred of the above compounds.

One aspect of the present invention is a composition comprising a latex having incorporated therein Compound 2. Preferred compositions are those wherein R' is methyl or phenyl and wherein n is 1 or 2 and m is 0. Preferably, Ar is selected from the group consisting of 5-member and 6-member aromatic and heteroaromatic rings. In a preferred embodiment Ar is phenyl substituted with an electron donating group at a position of the phenyl that is meta or para to the carbon that is bonded to the double bond and Ar' is phenyl. Exemplary compositions are those containing a compound selected from the group consisting of Compounds 9–16. The latex particles are usually suspendible and have an average diameter of 0.04 to 4000 nanometer. For assays the particle will have an spb member bound to it and will have an average diameter of 100 to 1000 micrometers.

Another embodiment of the present invention is a method for determining an analyte. The method comprises (a) providing in combination (1) a medium suspected of containing an analyte, (2) a photosensitizer capable in its excited state of activating oxygen to a singlet state, the photosensitizer associated with a specific binding pair (sbp) member, and (3) a suspendible latex particulate material comprising Compound 2. The particulate material has bound thereto an sbp member. The combination is treated with light, usually by irradiation, to excite the photosensitizer, and is then examined for the amount of luminescence emitted. The amount of such luminescence is related to the amount of analyte in the medium. The photosensitizer may be incorporated in a second suspendible particulate material. Particularly useful compositions for determining an analyte in accordance with the present invention are those containing Compound 1.

In the assay protocol the components are provided in combination and the light produced as a function of activation of oxygen by the sensitizer will be a function of analyte concentration. Advantageously, the methods of the present invention can be carried out without heating the medium to produce light. Consequently, the assay of the present invention can be conducted at a constant temperature.

The chemiluminescent compound may be bound to a sbp member that is capable of binding directly or indirectly to the analyte or to an assay component whose concentration is affected by the presence of the analyte. The term "capable of binding directly or indirectly" means that the designated entity can bind specifically to the entity (directly) or can bind specifically to a specific binding pair member or to a complex of two or more sbp members which is capable of binding the other entity (indirectly). Preferably, assays conducted in accordance with the present invention utilize one of the above compositions in a latex particle. This latex particle has an sbp member generally capable of binding directly or indirectly to the analyte or a receptor for the analyte. When the sbp members associated with the photosensitizer and the chemiluminescent compound are both capable of binding to the analyte, a sandwich assay protocol results. When one of the sbp members associated with the photosensitizer or chemiluminescent compound can bind both the analyte and an analyte analog, a competitive assay protocol can result.

The photosensitizer is usually caused to activate the chemiluminescent compound by irradiating the medium containing the above reactants. The medium must be irradiated with light having a wavelength with energy sufficient to convert the photosensitizer to an excited state and thereby render it capable of activating molecular oxygen to singlet oxygen. The excited state for the photosensitizer capable of exciting molecular oxygen is generally a triplet state which is more than about 20, usually at least 23, Kcal/mol more energetic than the photosensitizer ground state. Preferably, the medium is irradiated with light having a wavelength of about 450 to 950 nm although shorter wavelengths can be used, for example, 230–950 nm. The luminescence produced may be measured in any convenient manner such as photographically, visually or photometrically to determine the amount thereof, which is related to the amount of analyte in the medium.

Although it will usually be preferable to excite the photosensitizer by irradiation with light of a wavelength that is efficiently absorbed by the photosensitizer, other means of excitation may be used as for example by energy transfer from an excited state of an energy donor such as a second photosensitizer. When a second photosensitizer is used, wavelengths of light can be used which are inefficiently absorbed by the photosensitizer but efficiently absorbed by the second photosensitizer. The second photosensitizer may be bound to an assay component that is associated, or becomes associated, with the first photosensitizer, for example, bound to a surface or incorporated in the particle having the first photosensitizer. When a second photosensitizer is employed it will usually have a lowest energy singlet state at a higher energy than the lowest energy singlet state of the first photosensitizer.

The 632.6 nm emission line of a helium-neon laser is an inexpensive light source for excitation. Photosensitizers with absorption maxima in the region of about 620 to about 650 nm are compatible with the emission line of a helium-neon laser and are, therefore, particularly useful in the present invention.

The method and compositions of the invention may be adapted to most assays involving sbp members such as ligand-receptor; e.g., antigen-antibody reactions; polynucleotide binding assays, and so forth. The assays may be homogeneous or heterogeneous, competitive or noncompetitive. The assay components, chemiluminescent compound and photosensitizer, can be utilized in a number of ways with (1) a surface, when employed, (2) nucleic acid or receptor and (3) nucleic acid or ligand. The association may involve covalent or non-covalent bonds. Those skilled in the art will be able to choose appropriate associations depending on the particular assay desired in view of the foregoing and the following illustrative discussion.

In a homogeneous assay approach, the sample may be pretreated if necessary to remove unwanted materials. The reaction for a noncompetitive sandwich type assay can involve an sbp member, (e.g., an antibody, nucleic acid probe, receptor or ligand) complementary to the analyte and associated with a chemiluminescent compound; a photosensitizer associated with an sbp member, (e.g., antibody, nucleic acid probe, receptor or ligand) that is also complementary to the analyte; the sample of interest; and any ancillary reagents required. Preferably, at least the chemiluminescent compound is incorporated in particles to which an sbp member is attached. The photosensitizer may be directly attached to an sbp member or it may also be incorporated into particles. In a competitive protocol one sbp member can be a derivative of the analyte and the other sbp member can be complementary to the analyte, e.g., an antibody. In either protocol the components may be combined either simultaneously or wholly or partially sequentially. The ability of singlet oxygen produced by an activated photosensitizer to react with the chemiluminescent compound is governed by the binding of an sbp member to the analyte. Hence, the presence or amount of analyte can be determined by measuring the amount of light emitted upon activation of the photosensitizer by irradiation, heating or addition of a chemical reagent, preferably by irradiation. Both the binding reaction and detection of the extent thereof can be carried out in a homogeneous solution without separation. This is an advantage of the present invention over prior art methods utilizing chemiluminescence.

In a heterogeneous assay approach, the assay components comprise a sample suspected of containing an analyte which is an sbp member; an sbp member bound to a support, which may be either a non-dispersible surface or a particle having associated with it one member of a group consisting of the chemiluminescent compound and the photosensitizer; and an sbp member having the other member of the group associated with it wherein the sbp members can independently, either directly or indirectly, bind the analyte or a receptor for the analyte. These components are generally combined either simultaneously or wholly or partially sequentially. The surface or particles are then separated from the liquid phase and either the separated phase or the liquid phase is subjected to conditions for activating the photosensitizer, usually by irradiating the particular phase in question, and measuring the amount of light emitted.

The binding reactions in an assay for the analyte will normally be carried out in an aqueous medium at a moderate pH, generally that which provides optimum assay sensitivity. Preferably, the activation of the photosensitizer will also be carried out in an aqueous medium. However, when a separation step is employed, non-aqueous media such as, e.g., acetonitrile, acetone, toluene, benzonitrile, etc. and aqueous media with pH values that are very high, i.e., greater than 10.0, or very low, i.e., less than 4.0, usually very high, can be used. As explained above, the assay can be performed either without separation (homogeneous) or with separation (heterogeneous) of any of the assay components or products.

The aqueous medium may be solely water or may include from 0.01 to 80 volume percent of a cosolvent but will usually include less than 40% of a cosolvent when an sbp member is used that is a protein. The pH for the medium of the binding reaction will usually be in the range of about 4 to 11, more usually in the range of about 5 to 10, and preferably in the range of about 6.5 to 9.5. When the pH is not changed during the generation of singlet oxygen the pH will usually be a compromise between optimum binding of the binding members and the pH optimum for the production of signal and the stability of other reagents of the assay. When elevated pH's are required for signal production, a step involving the addition of an alkaline reagent can be inserted between the binding reaction and generation of singlet oxygen and/or signal production. Usually the elevated pH will be greater than 10, usually 10–14. For heterogenous assays non-aqueous solvents may also be used as mentioned above, the main consideration being that the solvent not react efficiently with singlet oxygen.

Various buffers may be used to achieve the desired pH and maintain the pH during an assay. Illustrative buffers include borate, phosphate, carbonate, tris, barbital and the like. The particular buffer employed is not critical to this invention, but in an individual assay one or another buffer may be preferred.

Moderate temperatures are normally employed for carrying out the binding reactions of proteinaceous ligands and receptors in the assay and usually constant temperature, preferably, 25 to 40, during the period of the measurement. Incubation temperatures for the binding reaction will normally range from about 5° to 45° C., usually from about 15° to 40° C., more usually 25° to 40° C. Where binding of nucleic acids occur in the assay, higher temperatures will frequently be used, usually 20 to 90, more usually 35° to 75° C. Temperatures during measurements, that is, generation of singlet oxygen and light detection, will generally range from about 20° to 100°, more usually from about 25° to 50° C., more usually 25° to 40° C.

The concentration of analyte which may be assayed will generally vary from about $10^{-4}$ to below $10^{-16}$M, more usually from about $10^6$ to $10^{14}$M. Considerations, such as whether the assay is qualitative, semiquantitative or quantitative, the particular detection technique the concentration of the analyte of interest, and the maximum desired incubation times will normally determine the concentrations of the various reagents.

In competitive assays, while the concentrations of the various reagents in the assay medium will generally be determined by the concentration range of interest of the analyte, the final concentration of each of the reagents will normally be determined empirically to optimize the sensitivity of the assay over the range. That is, a variation in concentration of the analyte which is of significance should provide an accurately measurable signal difference.

The concentration of the sbp members will depend on the analyte concentration, the desired rate of binding, and the degree that the sbp members bind nonspecifically. Usually, the sbp members will be present in at least the lowest expected analyte concentration, preferably at least the highest analyte concentration expected, and for noncompetitive assays the concentrations may be 10 to $10^6$ times the highest analyte concentration but usually less than $10^{-4}$M, preferably less than $10^{-6}$M, frequently between $10^{-11}$ and $10^{-7}$M. The amount of photosensitizer or chemiluminescent compound associated with a sbp member will usually be at least one molecule per sbp member and may be as high as $10^5$, usually at least $10$–$10^4$ when the photosensitizer or chemiluminescent molecule is incorporated in a particle.

While the order of addition may be varied widely, there will be certain preferences depending on the nature of the assay. The simplest order of addition is to add all the materials simultaneously. Alternatively, the reagents can be combined wholly or partially sequentially. When the assay is competitive, it will often be desirable to add the analyte analog after combining the sample and an sbp member capable of binding the analyte. Optionally, an incubation step may be involved after the reagents are combined, generally ranging from about 30 seconds to 6 hours, more usually from about 2 minutes to 1 hour before the sensitizer is caused to generate singlet oxygen and the light emission is measured.

In a particularly preferred order of addition, a first set of specific binding pair members that are complementary to and/or homologous with the analyte are combined with the analyte followed by the addition of specific binding pair members complementary to the first specific binding pair members, each associated with a different member of the group consisting of a photosensitizer and a composition of the present invention. The assay mixture, or a separated component thereof, is then irradiated and the light emission is measured.

In a homogeneous assay after all of the reagents have been combined, they can be incubated, if desired. Then, the combination is irradiated and the resulting light emitted is measured. The emitted light is related to the amount of the analyte in the sample tested. The amounts of the reagents of the invention employed in a homogeneous assay depend on the nature of the analyte. Generally, the homogeneous assay of the present invention exhibits an increased sensitivity over known assays such as the EMIT® assay. This advantage results primarily because of the improved signal to noise ratio obtained in the present method.

Another aspect of the present invention relates to kits useful for conveniently performing an assay method of the invention for determining the presence or amount of an analyte in a sample suspected of containing the analyte. The kits comprise in packaged combination: (1) a composition comprising a suspendible latex particle comprising a compound of the formula of Compound 2, preferably of Compound 1, where the particle can bind a specific binding pair (sbp) member, and (2) a photosensitizer capable in its excited state of activating oxygen to its singlet state. The photosensitizer can be part of a composition comprising a second suspendible particle comprising the photosensitizer where the second particle has bound thereto a sbp member or it may be directly bound to a sbp member. The kit can further include a written description of a method in accordance with the present invention and instructions for using the reagents of the kit in such method.

To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. The kit can further include other separately packaged reagents for conducting an assay including ancillary reagents, and so forth.

EXAMPLES

The invention is demonstrated further by the following illustrative examples. Parts and percentages used herein are by weight unless otherwise specified. Temperatures are in degrees centigrade (° C.).

Abbreviations:

$Ab_F$ (anti-fluorescein)—Mouse monoclonal antibody to fluorescein.
$Ab_{T3}$ (anti-$T_3$)—mouse monoclonal antibody to $T_3$
t-Bu—tert-butyl
TFA—trifluoroacetic acid
$T_3$—
Φ—chemiluminescence quantum yield
PMT—
EtoAc—ethyl acetate
BSA—Bovine serum albumin
Chl-a—Chlorophyll—a
D-$H_2O$—dionized water
DPP—4.7—Diphenylphenanthroline
DPPC—dipalmitoylphosphatidyl choline
DPPG—dipalmitoylphosphatidyl glycerol
DPPE—dipalmitoylphosphatidyl ethanolamine
EDAC—1-Ethyl-3-(3-Dimethylaminopropyl) carbodiimide hydrochloride.
$nC_{10}$—tetra-(n-decyl)phthalocyanin aluminum chloride complex.
PB—Polystyrene beads
PB/$nC_{10}$—PB containing $nC_{10}$
PBS—phosphate buffered saline 0.02M NaPi, 0.14M NaCl/ pH 7.2
Pi—Phosphate
Sulfo-NHS—Sulfo-N-hydroxysuccinimide
SATA—S-acetylthioglycolic acid N-hydroxysuccinimide ester
RLU—Relative light units.
NHS—N-hydroxysuccinimide
DMSO—dimethyl sulfoxide
DMF—dimethyl formamide
DCC—dicyclohexylcarbodiimide
TEA—triethylamine
TLC—thin layer chromatography
TNBSA—2.4.6-trinitrobenzenesulfonic acid
BGG—bovine gamma globulin
TMSCl—trimethylsilyl chloride
MeOH—methanol
Biotin-LC$_7$-NHS -sulfosuccinimidyl-6-(biotinamido)-hexanoate
λmax ABS—lambda maximum of absorption
λmax EMI—lambda maximum of fluorescence emission
λmax CH.EM.—lambda maximum of chemiluminescence emission All monoclonal antibodies were produced by standard hybrid cell technology. Briefly, the appropriate immunogen was injected into a host, usually a mouse or other suitable animal, and after a suitable period of time the spleen cells from the host were obtained. Alternatively, unsensitized cells from the host were isolated and directly sensitized with the immunogen in vitro. Hybrid cells were formed by fusing the above cells with an appropriate myeloma cell line and culturing the fused cells. The antibodies produced by the cultured hybrid cells were screened for their binding affinity to the particular antigen, e.g. TSH or HCG. A number of screening techniques were employed such as, for example, ELISA screens. Selected fusions were then recloned.

Example 1
Total Triiodothyronine Assay
I. Bead Preparations
Materials 175 nm Carboxylate modified latex (CML beads) from Bangs Laboratories.

Ethylene glycol, ethoxy ethanol, benzyl alcohol, chlorophyll-a from Aldrich.

Europium (III) thienoyl trifluoroacetonate (EuTTA) from Kodak.

Trioctyl phosphine oxide (TOPO) from Aldrich.

Dioxene |1-(4-dimethylaminophenyl)-6-phenyl 1,4 dioxene|:

Prepared by a modification of a procedure described in: Giagnon, S. D. (1982) University Microfilms International (Ann Arbor, Mich.)

Procedures

1. Chlorophyll-a Sensitizer Beads

A solution of chlorphyll-a in benzyl alcohol (1.0 mL, 0.6 mM) was added to 8.0 mL of benzyl alcohol at 105° C. A suspension of carboxylate modified latex, 175 nm size, in water (10%, 1.0 mL) was added to the benzyl alcohol solution. The mixture was stirred for 5 min at 105° C., and cooled to room temperature. Ethanol (10.0 mL) was added and the mixture centrifuged. The pellet was resuspended in a 1:1 ethanol-water mixture (10.0 mL) and the suspension centrifuged. The same resuspension and centrifugation procedure was repeated in water (10.0 mL), and the pellet was resuspended in water (1.8 mL).

Characterization

A. Dye concentration: A solution prepared by adding 10 µL of the above bead suspension to dioxane (990 µL) was found to have an absorbance of 0.11 at 660 nm, corresponding to 2.6µmoles of chlorophyll-a in one gram of beads.

B. Singlet oxygen generation: A mixture of chlorphyll-a beads (200 µg) $2 \times 10^{-4}$ moles of anthracene 9,10-dipropionic acid (ADPA) in two mL of phosphate buffer (50 mM, pH 7.5, containing 100 mM NaCl) was irradiated with a tungsten-halogen lamp equipped with a 645 rim cut-off filter for 20 min. The beads were removed by filtration, and the concentration of the oxygenation product was determined spectrophotometrically at 400 nm. The rate was found to be 3.0 nmoles of oxygenation product per min. Under the same conditions, 38 pmoles of a soluble sensitizer, aluminum phthalocyanin tetrasulfonate generated the same amount of oxygenation product (the amount of sensitizer in the beads was $200 \cdot 10^{-6} \cdot 2.6 \cdot 10^{-6} = 520$ pmoles).

2. Chlorophyll-a/Tetrabutyl Squarate Sensitizer Beads

A suspension of carboxylated latex beads (175 nm size, 10% solids in water, 30.0 mL) was centrifuged. The supernatant was discarded and the pellet was resuspended in ethylene glycol (60.0 mL). The suspension was heated to 100° C. 9.0 mL of a benzyl alcohol solution which is 1.67 mM in chlorophyll-a and 3.33 mM in tetrabutyl squarate |1,3 bis(4-dibutylaminophenyl)squarate| was added slowly over 3 min to the suspension. The heating was continued for 7 min, then the suspension was cooled to room temperature in a water bath. The benzyl alcohol suspension was added to cold ethanol (120 mL). The mixture was centrifuged and the supernatant discarded. The pellet was resuspended in 50% ethanol in water and the suspension was centrifuged. The same resuspension and centrifugation procedure was repeated in 5% ethanol in water (30 mL))

Characterization

A. Dye concentration. The concentration of the tetrabutyl squarate in the beads was determined spectrophotometrically as described above for the chlorophyll-a beads. It was found to be 44 µM dye in the beads.

B. Singlet oxygen generation. Twenty-five µL of a 5 mM solution of ADPA in ethanol were added to suspension of beads (100 µg) in phosphate buffer, pH 7.0 (20 mM, containing 50 mM NaCl). The mixture was irradiated as above, using a 610 nm long pass filter. The rate of singlet oxygen formation was calculated from the rate of the decrease in absorbance (at 400 nm) of the ADPA. It was found that the beads generated $7 \cdot 10^{-2}$ µmoles of singlet oxygen/min.

3. Dioxene/EuTTA/TOPO Acceptor Beads 20 mL of 175 nm carboxylated latex beads (10% suspension in water) was added to ethoxy ethanol (20.0 mL). The mixture was heated to 90° C. 20 mL of a solution which is 10 mM 2-(p-dimethylaminophenyl)-3-phenyl dioxene, 20 mM EUTTA and 60 mM TOPO in ethoxy ethanol were added to the mixture. The heating was continued for 7 min at a temperature up to 97° C. The mixture was cooled to room temperature. Ethanol (40.0 mL) was added and the mixture was centrifuged. The pellet was resuspended in 80% ethanol and the suspension was centrifuged. The resuspension and centrifugation procedure was repeated in 10% ethanol (36 mL).

Characterization

A. Dye concentration. The concentration of EuTTA in the beads was determined spectrophotometrically and was found to be 0.07M. Because the concentration of dioxene cannot be determined in the presence of EuTTA, it was measured in beads which were dyed with the dioxene only, 2-(p-dimethylaminophenyl)-3-phenyl dioxene, under the same conditions. The concentration was found to be 0.016M.

B. Signal generation. A suspension of beads (25 µg) in phosphate buffer (0.5 mL, 20 mM phosphate, 50 mM NaCl, 0.1% Tween 20, pH 7.0) was mixed with a solution of 2 µM aluminum phthalocyanine tetrasulfonate (0.5 mL) in the same buffer. The mixture was illuminated for one minute with a 125 w tungsten-halogen lamp equipped with a 610 nm long pass filter. Following illumination, the mixture was placed in a Turner TD-20e luminometer, and the luminescence was measured for 20 sec. The intensity was found to be 327 RLU (relative light unit)/sec. The wavelength of the emitted light was measured using Perkin-Elmer 650-40 scanning spectrofluorimeter. The major emission peak was centered near 615 nm.

II. Assay Procedure EDAC/NHS Coupling of Antibody to 40 nm Beads 73.6 mg sulfo-NHS (N-hydroxysulfo-succinimide, Pierce Chemical Co. #24510 G) was dissolved in 6 mL of a suspension of 4 mg/mL carboxylate-modified 40 nm polystyrene beads (dyed with chlorophyll-a and tetrabutyl squarate) in water. 136 uL 0.5M $Na_2HPO_4$ was added. PH was adjusted to 5.2. 136 uL additional water was added. 130.4 mg EDAC (1-ethyl-3-(3-dimethylaminopropyl) carbodiimide hydrochloride, Sigma Chemical Co. #E-6383) in 454 µL water was slowly added to stirring bead suspension. The suspension was incubated for 20 min at room temperature. The beads were centrifuged for 20 min. at 15,000 rpm in Sorvall SA-600 rotor at 4° C. The supernatant was discarded. The beads were then resuspended in 1.2 mL 5 mM sodium phosphate, pH 5.8, and the suspension was sonicated to redisperse beads. The beads were slowly added to 4.8 mL of a stirring solution containing 1.7 mg/mL IgG (mouse monoclonal anti-fluorescein) and 6.7 mg/mL BSA and 17 mM borax, pH 9.2, and mixed gently overnight at 4° C. 800 µL 2M glycine was added which was then followed by 2.8 mL 50 mg/mL BSA in 0.1M borax to the bead suspension. The suspension was sonciated and allowed to mix gently for 3 h at 4° C. The beads were centrifuged for 30 min at 15,000 rpm. The supernatant was discarded. The beads were resuspended in 3 mL 50 mM sodium phosphate and 150 mM NaCl, pH 7.6, and the suspension was sonciated. The centrifugation, resuspension and sonification steps were repeated for a total of three spins. After the third spin, Assay Protocol 50 µL of 8-anilino-1-naphthalene sulfonic acid, ammonium salt (Sigma, A-3125) solution in assay buffer (0.75 mg/mL) was added to 50 µL of $T_3$ standard or sample. 100 µL of assay buffer was added. Biotinylated anti-$T_3$ was prepared according to standard procedures by reaction of biotin-$LC_7$NHS (Pierce Chemical Company) with monoclonal anti-$T_3$ followed by purification by chromatography on a Sephadex column. 50 µL of biotinylated anti-$T_3$ (70 ng/mL) in assay buffer was added. The tracer, $T_3$-$LC_{21}$-Fl (1.8 ng/mL)

$T_3$-$LC_{21}$-Fl

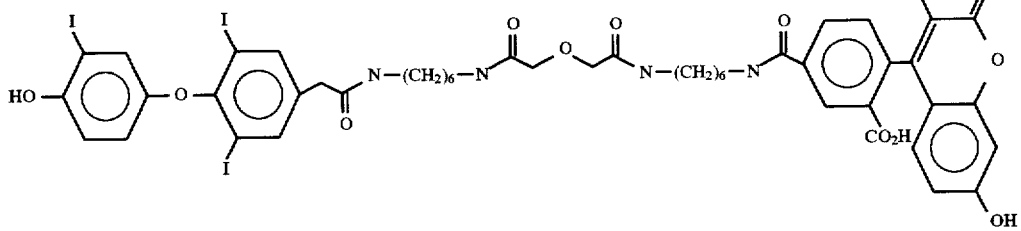

beads were resuspended in 2.4 mL 50 mM sodium phosphate and 150 mM NaCl, pH 7.6. The resulting suspension was sonicated and stored at 4° C.

III. EDAC/NHS Coupling of Avidin-D to 175 nm Beads 4.4 mg sulfo-NHS was dissolved in 0.4 mL of a suspension of 25 mg/mL carboxylate-modified 175 nm polystyrene beads (dyed with 2-(p-dimethylaminophenyl)-3-phenyl dioxene/Eu(TTA)/TOPO) in water. 0.0160 mL 0.25M $Na_2HPO_4$ was added. 8 mg EDAC, dissolved in 0.030 mL water, was added slowly to vortexing bead suspension. The suspension was incubated for 20 min at room temperature. The beads were centrifuged 20 min at 15,000 rpm in Sorvall SA-600 rotor at 4° C. The supernatant was discarded. The beads were resuspended in 0.6 mL 0.005M sodium phosphate, pH 5.8. The suspension was sonicated to resuspend beads. The beads were again slowly added to 3 mL of a stirring solution containing 1.33 mg/mL avidin-D (Vector) and 17 mM borax, pH 9.2, and mixed gently overnight at 4° C. 0.004 mL 1M succinic anhydride in DMF was added. The suspension was incubated for 1 h at 4° C. with gentle mixing. 0.4 mL 50 mg/mL BSA in 10 mM sodium phosphate and 150 mM NaCl, pH 7.0 was added. The suspension was allowed to mix gently for 3 h at 4° C. The beads were centrifuged for 30 min at 15,000 rpm. The supernatant was discarded. The beads were resuspended in 3 mL 50 mM sodium phosphate and 150 mM NaCl, pH 7.6. The suspension was sonicated. The centrifugation, resuspension and sonification steps were repeated for a total of three spins. After the third spin, the beads were resuspended in 2.25 mL 50 mM sodium phosphate and 150 mM NaCl, pH 7.6. The suspension was sonicated and stored at 4° C.

IV. Total $T_3$ Assay Assay buffer: 0.075M barbital, 0.2M NaCl, 0.4% BSA, 1.25% mouse IgG, 10 mg/mL dextran sulfate (MW 500,000), 1.0 mg/mL dextran T-500, 10 µg/mL aggregated IgG.

Beads

Acceptor Beads: Avidin-EDAC, 175 nm, dyed with 2-(p-dimethylaminophenyl)-3-phenyl dioxene/Eu(TTA)$_3$/TOPO. Sensitizer Beads: Antifluorescein-EDAC, 40 nm, dyed with chlorophyll-a/squarate.

in assay buffer (50 µL) was added. The mixture was incubated for 15 minutes at 37° C. 500 µL of a suspension of sensitizer beads (50 µg) and acceptor beads (6.25 µg) in assay buffer were added, and the mixture was incubated for 15 minutes at 37° C. The "stop solution" (50 µL) (10 µM fluorescein, 0.5 mM biotin) was added.

Signal was read by halogen lamp with a 610 nm cut-off filter, one minute illumination, 20 sec measurement.

Results

The luminescence signal was plotted as a function of $T_3$ concentration. Signal modulation was 94% with 8.5 ng/mL $T_3$. At 0.5 ng/mL the signal modulation was 38%.

Example 2

Chemiluminescence Quantum Yield and Decay Rate Determinations

Preparation of Compound 11

To a stirred solution of 2.55 g of 4-dimethylaminobenzoin (10 mmol) in 50 mL of dry toluene, 1.2 mL of 2-mercaptoethanol (15 mmol) was added, followed by 2.5 mL of TMSCl. The reaction mixture was refluxed under argon for 18 hours, allowed to come to room temperature and poured in 150 mL of saturated bicarbonate solution. The two-phase mixture was separated. The organic layer was again washed with 100 mL of saturated bicarbonate solution. The combined aqueous layer was extracted with 75 mL of $CH_2CL_2$. The combined organic layers were dried over sodium sulfate (20 g) and evaporated. The remaining residue was flash chromatographed ($CH_2Cl_2$) to give 2.6 g of Compounds 11 and 20 (4:1 mixture of the 2-regioisomers). The ash colored solid was recrystallized from $CH_2Cl_2$-MeOH (10:90) mixture to yield 1.8 g of needle-shaped crystals of a single regioisomer of compound 11.

M.P. 108 - 110° C.; [1] HNMR (CDCl$_3$, 250 MHz): δ2.85 (s, 6H), 3.22 (t, 2H), 4.5 (t, 2H), 6.55 (d, 2H), 7.1–7.3 (m, 7H).

Mass Spectrum (CI: m/e, relative intensity) Major Peaks: 297 ($M^+$, 40), 165 (100).

Absorption Spectra (Toluene): 330 nm (ε 13,000).

Photooxygenation Procedure

25 Milligrams of Compound 11 (major regioisomer from above) was dissolved in 10 mL of $CH_2Cl_2$ in a photooxygenation tube. Approximately 50 mg of polystyrene bound Rose Bengal was added and oxygen bubbler connected. Oxygen was passed slowly through the solution while the sample as irradiated with a Dolan-Jenner lamp equipped with a 500 nm cut-off filter. Progress of the reaction was monitored by TLC. A spot for the thioester product could be detected and had a lower $R_f(CH_2Cl_2)$ than Compound 11. The reaction was judged complete when Compound 13 was completely consumed. The sensitizer was filtered off and solution was evaporated on a rotary evaporator to yield 26 mg of thioester 32 as the only product.

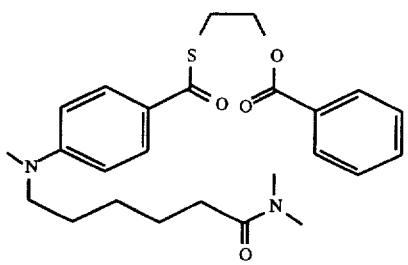

(32)

1HNMR: $(CD_2CL_2)$ : δ 3.05 (s, 6H) , 3.4 (5, 2H) 4.45 (5, 2H) , 6.72 (d, 2H) , 7.5 (m, 3H) , 7.85 (d, 2H) , 8.05 (d, 2H).

Mass Spectra (CI, relative intensity) Major Peaks: 329 ($M^+$, 25) , 148 (100).

Absorption Spectrum $(CH_2Cl_2)$: 342 nm (~30,000).

Fluorescence Spectrum (Toluene): 370 nm.

Fluorescence Measurements

A solution of thioester 32 was taken in four different solvents (Toluene-dry; $CH_2Cl_2$; hexane; and acetonitrile) and placed in a 1-cm square quartz cuvette in the sample compartment of a Perkin-Elmer 650-40 fluorometer. The sample was excited at the absorption maxima of each solvent (slit width 2 nm) and emission spectra (slit width 3 nm) was recorded by scanning from 350 nm to 470 nm. The fluorescence efficiency was determined and tabulated in Table 1.

TABLE 1

Efficiency of Thioester in Different Solvents

| Compound | Solvent | λ ABS nM | λ EMI nM | Φ |
|---|---|---|---|---|
| Diester* | Toluene | 314 | 360, 400 | 0.1 |
| Thioester 32** | Toluene | 338 | 370 | 0.025 |
| | $CH_2Cl_2$ | 340 | 390 | 0.07 |
| | Hexane | 332 | 370 | ~0.006 |
| | CHCN | 342 | 390 | ~0.006 |

*2-(p-dimethylaminophenyl)3-phenyl ethyldiester, Giagnon, S. D. (1982) University Microfilms International (Ann Arbor, Michigan).
**Thioester is rapidly photobleached on excitation at 340 nm in toluene.

Determination of Quantum Yield of Chemiluminescence.

Preparation of Eu(TTA)Phen:

8.69 g of $Eu(TTA)_3 \cdot 3H_2O$ (10 mmoles, Kodak) and 1.8 g of 1,10-phenanthroline (10 mmoles, Aldrick) in 50 ml of dry toluene were heated to 95° C. in an oil bath for one 1 hour. Toluene was removed under reduced pressure. The ash coloured solid was cystallized from 10 ml of toluene to yeild 10 grams of $Eu(TTA)_3Phen$.

Absorption spectrum: 270 nm (20,000), 340 nm (60,000) (Toluene); 1.R(KBr): $Cm^{-1}$: 3440(s), 1600(s), 1540(s), 1400 (s), 1300(s)

Energy Transfer to $Eu(TTA)_3Phen$

A solution of Compound 11 (regioisomers from above) (0.1 mM) (8:2 mixture), aluminum phthalocyanine (0.1 µM), and $Eu(TTA)_3Phen$ from above (0–4.0 mM) in dry toluene was placed in a 1-cm square quartz cuvette (two sided silvered) in the sample compartment of a Spex Fluorolog spectrophotometer. The temperature of the sample holder was maintained by a circulating external water bath at 25° C. A 640 nm cut-off filter was placed in front of the excitation beam. The sample solutions were placed in the sample compartment for at least 3 minutes for thermal equilibrium to be reached. The emission was recorded in the time drive mode. Samples were irradiated at 680 nm (slit width 24 nm) until a steady state of emission at 613 nm (slit width 8 nm) was reached. The steady state light intensity at various concentrations of $Eu(TTA)_3Phen$ was recorded and is summarized in Table 2. From the steady state light intensity quantum yields were determined. Double reciprocal plots of chemiluminescence intensity against $Eu(TTA)_3Phen$ concentration were linear.

TABLE 2

Chemiluminescence Efficiency as a Function of $Eu(TTA)_3Phen$ Concentration

| Compound 11* mM | $Eu(TTA)_3Phen$ mM | RLU at 613 nm |
|---|---|---|
| 0.1 | 0 | — |
| 0.1 | 0.05 | $7.43 \times 10^4$ |
| 0.1 | 0.1 | $1.8 \times 10^5$ |
| 0.1 | 0.2 | $2.89 \times 10^5$ |
| 0.1 | 0.5 | $6.13 \times 10^5$ |
| 0.1 | 1.0 | $9.45 \times 10^5$ |
| 0.1 | 2.0 | $1.17 \times 10^6$ |
| 0.1 | 4.0 | $1.32 \times 10^6$ |
| 0.1** | 4.0 | $1.6 \times 10^6$ |

*Except for last run Compound 11 used in these experiments contained 20% of its regioisomer 20
**Compound 11 used in this experiment was greater than 98% of a single regioisomer.

Chemiluminescence from Dioxene 9

Experiment 1: A solution of dioxene 9 (0.1 mM) and aluminum phthalocyanine (0.1 µM) in dry toluene was irradiated at 680 nm as described above. The emission in light intensity at 400 nm (slit width 8 nm) was recorded as a function of irradiation time. The light intensity was 8793 RLU's for 180 seconds of irradiation (average of three experiments).

Experiment 2: Rate of dioxene 9 dioxetane decomposition was monitored by decay of chemiluminescence of an aerated solution in dry toluene at 25° C. Rate of decomposition was monitored in the presence of 1.0 µM aluminum phthalocyanine and dioxene (less than 0.1 mM of dioxene). The chemiluminescence decay was monitored on Spex Fluorolog spectrophotometer under previously described conditions. The rate constant of decay at 25° C. was $2.88 \times 10^{-4}$ $S^{-1}$.

Preparation of Acceptor Beads

Four mL of 20% suspension (400 mg) of washed 175 nm carboxylate modified latex was diluted with 3 mL of ethoxyethanol in a 25 mL round bottom (R.B.) flask with a stir bar. The R.B. flask was then placed in an oil bath at 105° C. and stirred for 10 minutes. Then, 3.3 mM thioxene 11 and 15.5 mM $Eu(TTA)_3DPP$ was added; the beads were stirred for 5 minutes more. At this point 1.0 mL of 0.1N NaOH was added slowly over 5 minutes. During all the additions, the oil bath temperature was maintained at 105° C. The oil bath temperature was slowly allowed to drop to room temperature over 2 hours.

After cooling, the mixture was diluted with 20 mL of ethanol and centrifuged (12,500 rpm, 30 minutes). Supernatants were discarded and the pellets resuspended in ethanol by sonication. Centrifugation was repeated, and the pellet was resuspended in water; and centrifugation was repeated. The pellet was resuspended in 5 mL of aqueous ethanol to a final volume of 40 mL. The final concentration of the beads was 10 mg/mL.

The concentration of Eu(TTA)$_3$DPP was determined spectrophotometrically. An aliquot of the bead suspension was reduced to dryness under a stream of dry argon and the residue dissolved in dioxane. Using a density of 1.06 g/cc for polystyrene, ($\epsilon$340 nm=6.7×10$^4$) for Eu(TTA)$_3$ and ($\epsilon$270 nm=4.0×10$^4$) for DPP, the concentration of Eu(TTA)$_3$DPP was determined to be 100 mM. The concentration of compound 11 in the beads could not be determined because its absorbance was masked by Eu(TTA)$_3$DPP.

Chemiluminescence of the beads was measured in an ORIEL luminometer using water-soluble aluminum phthalocyanine sensitizer. An aliquot of beads was diluted to 100 μg/mL in phosphate buffer pH 8.0 containing 0.1% Tween-20. 1.0 μM of aluminum phthalocyanine tetrasulfonic acid was added and chemiluminescent signal was measured as a function of irradiation time. An identical sample was also placed in a Spex Fluorolog fluorometer and irradiated at 680 nm (slit width 20 nm; 640 cut-off filter). The chemiluminescence emission spectra was recorded by scanning from 570 nm to 620 nm. Chemiluminescence decay and quantum yields is summarized in Table 3.

Determination of Quantum Yields in Beads

Dioxene 9 Beads

A solution of dioxene 9 beads (0.2 mg) and aluminum phthalocyanine tetrasulfonic acid (2.5 μM) in phosphate buffer (pH 8.2; 50 mM 0.1% Tween-20) was placed in a 1 cm quart cuvette (two sides silvered) in the sample compartment of a Spex Fluorolog spectrophotometer. The temperature of the sample holder was maintained 25° C. A 640 cut-off filter was placed in front of the excitation beam. The sample solutions were placed in the sample compartment for at least 3 minutes for thermal equilibrium to be reached. The light emission at 360 nm was followed in the time drive mode. Samples were irradiated at 680 nm (slit width 24 nm) for 60 seconds. The emission at 360 nm (slit width 16 nm) was recorded with time for 5000 seconds. Total light emitted was determined by the cut-weigh method. Peak shape correction was also done by the cut and weigh method. The total light emitted at 360 nm was 8.87±0.2×10$^4$ RLU's/4500 seconds (after peak shape correction; average of 2 experiments).

Dioxene 9: Eu(TTA)$_3$TOPO Beads

A solution of dioxene 9 Eu(TTA)$_3$TOPO beads (0.2 mg) and aluminum phthalocyanine tetrasulfonic acid (2.5 μM) in phosphate buffer (pH 8.2, 50 mM 0.1% Tween-20) was placed in a 1-cm quartz cuvette (two sides silvered) in the sample compartment of a Spex Fluorolog spectrophotometer. The rest of the experiment was performed as described for dioxene 9 beads. The light emission from beads was followed at 613 nm (slit width 16 nm).

Total light emitted was determined by the cut and weigh method. PMT correction was done as described previously in solution studies. The total light emitted at 613 nm was 25.0±0.3×10$^5$ RLU's/4500 seconds (after PMT correction; average of 2 experiments)

Steady State Methods

Dioxene 9: Eu(TTA)$_3$TOPO Beads. A solution of dioxene 9: Eu(TTA)$_3$TOPO beads (0.5 mg) and aluminum phthalocyanine tetrasulfonic acid (0.05 μM) in phosphate buffer (pH 8.2; 50 mM 0.1% Tween-20) was placed in a 12–75 mM test tube in the sample compartment of an Oriel chemiluminometer. The temperature of the sample holder is 37° C. A 610 cut-off filter was placed in front of the excitation beam. The sample solutions were placed in the sample compartment for at least 5 minutes for thermal equilibrium to be reached. The sample was irradiated for 30-second intervals followed by a 5-second read time until a steady state of emission is reached. The average intensity at steady state emission is 21,000±1000 RLU's (3 experiments).

Compound 11: Eu(TTA)$_3$DPP Beads. A solution of thioxene 11: Eu(TTA)$_3$DPP beads (0.5 mg) and aluminum phthalocyanine tetrasulfonic acid (0.05 μM) in phosphate buffer (pH 8.2, 50 mM, 0.1% Tween-20) was placed in 12–75 mM test tube in the sample compartment of an Oriel chemiluminometer. The temperature of the sample holder is 37° C. A 610 cut-off filter was placed in front of the excitation beam. The sample solutions were placed in the sample compartment for at least 5 minutes for thermal equilibrium to be reached. The sample was irradiated for 6-second intervals followed by 3 seconds read time until a steady state of emission was reached. The average intensity at steady state emission is 32,000±1000 (3 experiments).

TABLE 3

Chemiluminescent Properties of Thioxene 11 and Dioxene 9

| Compound | Medium | λmax (CH.EM) | t½ | Φ |
| --- | --- | --- | --- | --- |
| 11 (100 μM) | Toluene | 400 nM | 2.1 sec | low* |
| 11 + Eu(TTA)$_3$Phen (4 mM) | Toluene | 613 nM | 1.8–2.1 sec | 0.20*** |
| 11 + Eu(TTA)$_3$DPP (100 mM) | CML beads | 613 nM | decay multiphasic (initial t½ at 37° C. is ~0.5 secs) | 0.46 |
| 9 (100 μM) | Toluene | 420 nM | 3462 sec | 0.015 |
| ** | CML beads | 360 nM | decay multiphasic | 0.008 |
| 9 + Eu(TTA)$_3$.TOPO (16 mM) | CML beads | 613 nM (Major) 400 nM | decay multiphasic | 0.31 |

*less than 0.0003
**Control, no compound present
***0.37 for Eu(TTA)$_3$Phen concentration extrapolated to infinity Example 3

Preparation of C-26 Thioxene (Compound 13):

A. 62 g of N-methyl aniline (0.5 mole) and 62 g of ethyl 5-bromovalerate (0.3 mole) were heated to 100° C. in a sealed tube for 16 hours. The reaction mixture was cooled to room temperature and poured into 100 ml of ethyl acetate. The ethyl acetate solution was washed with 20% sodium hydroxide (3×100 ml). The aqueous layer was extracted with 50 ml of ethyl acetate. The combined ethyl acetate solution was dried over sodium sulphate (50 g) and removed under reduced pressure. The residue was distilled under high vacuum (130°–137° C.) to yield 60 g of N-methyl N-ethyl valerate aniline.

$^1$H NMR (CDCl$_3$, 250 MHz) : δ1.3 (t, 3H), 1.65 (m, 4H), 2.3 (t, 2H), 2.8 (s, 3H), 3.3 (t, 2H), 4.2 (q, 2H), 6.65 (d, 2H), 7.2 (m, 3H).

B. To a stirred solution of DMF (8.8 g) in an ice bath POCl₃ (5.06 g) was added slowly. After the addition was complete, the reaction is stirred at 4° C. for 10 minutes. N-methyl N- ethyl valeroyl aniline from Part A above (3.76 g) was added and the reaction was heated to 100° C. for 1 hour. The reaction mixture was poured into ice and neutralized with 20% sodium hydroxide. The mixture was extracted with ethyl acetate (3×50 ml). The combined ethyl acetate solution was dried over sodium sulphate (50 g) and removed under reduced pressure. The residue was passed through silica gel (CH₂Cl₂→ CH₂Cl₂:EtOAc 9:2).

¹H NMR (CDCl₃, 250 MHz): δ1.2 (t, 2H), 1.6 (m, 4H), 2.3 (t, 2H), 2.9 (s, 3H) 3.3 (t, 2H), 4.1 (q, 2H), 6.6 (d, 2H), 7.6 (d, 2H), 9.7 (s, 1H).

C. To a refluxing solution of 5.0 g of N-methyl N-ethyl-ω-valeroyl p-formyl aniline from Part B above (20 mmole) and 2 g of potassium cyanide in 60% ethanol under argon was added 2.15 g of benzaldehyde (20 mmole) in 20 ml of ethanol in 90 minutes. The reaction mixture was refluxed for 15 minutes more and extracted with ethyl acetate (3×50 ml). The combined ethyl acetate solution was dried over sodium sulphate (50 g) and removed under reduced pressure. The product was purified on preparative TLC (hexane: ethyl acetate 5:1) to yield 2.2 g of substituted benzoin.

¹H NMR (CDCl₃, 250 MHz): δ1.3 (t, 3H), 1.6 (m, 4H), 2.4 (t, 2H), 2.9 (s, 3H), 3.3 (t,2H), 4.1 (q, 2H), 4.8 (d, 1H), 5.8 (d, 1H), 6.5 (d, 2H), 7.3 (m, 5H), 7.8 (d, 2H).

D. To a stirred solution of the benzoin from Part C above (1.1 g) in 15 ml of ethanol was added 7 ml of water and 100 mgs of KOH. The reaction was stirred at room temperature for 3 hours. TLC (silica gel , CH₂Cl₂:EtOAc 9:1) showed no starting material. The solvent was neutralized and the carboxylic acid product was extracted with ethyl acetate (5×50 ml). The combined ethyl acetate solution was dried over sodium sulphate (50 g) and removed under reduced pressure. The carboxylic acid product was used as is for the next step.

¹H NMR (CDCl₃, 250 MHz) : δ1.6 (m, 4H), 2.4 (t, 2H), 2.9 (s, 3H), 3.3 (t, 2H), 5.8 (s, 1H), 6.5 (d, 2H), 7.3 (m, 5H), 7.8 (d, 2H).

E. To a stirred solution of the carboxylic acid from Part D above (1.7 g, 5 mmole) and didecyl amine (1.9 g, 6.3 mmole) in 80 ml of DMF at 4° C. was added DPPA (1.8 g, 8 mmole) followed by addition of triethyl amine (1.25 ml). The reaction mixture was stirred at 4° C. and then at room temperature for 16 hours. The solvent was neutralized and the product was extracted with ethyl acetate (5×50 ml). The combined ethyl acetate solution was dried over sodium sulphate (50 g) and removed under reduced pressure. The product was purified on preparative TLC (CH₂Cl₂: ethyl acetate 9:1) to yield 2.6 g of substituted amide benzoin.

¹H NMR (CDCl₃, 250 MHz) : δ0.8 (t, 6H), 1.3 (m, 36H), 1.6 (m, 12H), 2.3 (t, 2H), 2.7 (m, 4H), 3.0 (s, 3H), 3.3 (m, 6H), 4.8 (d, 1H), 5.8 (d, 1H), 6.5 (d, 2H) , 7.3 (m, 5H) , 7.8 (d, 2H).

F. To a stirred solution of 1.5 g of substituted benzoin (2.5 mmole) in 50 ml of dry toluene, 1.2 ml of 2-thioethanol (15 mmole) was added, followed by 2.5 ml of TMSCl. The reaction mixture was refluxed in an oil bath under argon for 30 hours. The reaction mixture was allowed to come to room temperature poured into 150 ml of saturated bicarbonate solution. The organic layer was separated and washed with 100 ml of saturated bicarbonate solution. The combined aqueous layer was extracted with 75 ml of CH₂Cl₂.

The combined organic solution was dried over sodium sulphate (50 g) and removed under reduced pressure.The product was purified on silica gel (CH₂Cl₂: ethyl acetate 9:1) to yield 1.2 g of C-26 thioxene as an pale yellow oil.

¹H NMR (CDCl₃, 250 MHz) : δ0.8 (t, 6H), 1.3 (m, 36H), 1.6 (m, 12H), 2.3 (t, 2H), 2.8 (s, 3H), 3.3 (m, 9H), 4.5 (t, 2H), 6.5 (d, 2H), 7.1 (d, 2H), 7.3 (m, 5H).

Mass Spectrum (CI: m/e) M⁺662.

Absorption Spectra (Toluene) : 330 nm (ε13,000).

Example 4
Preparation of C-8 Thioxene (Compound 15):

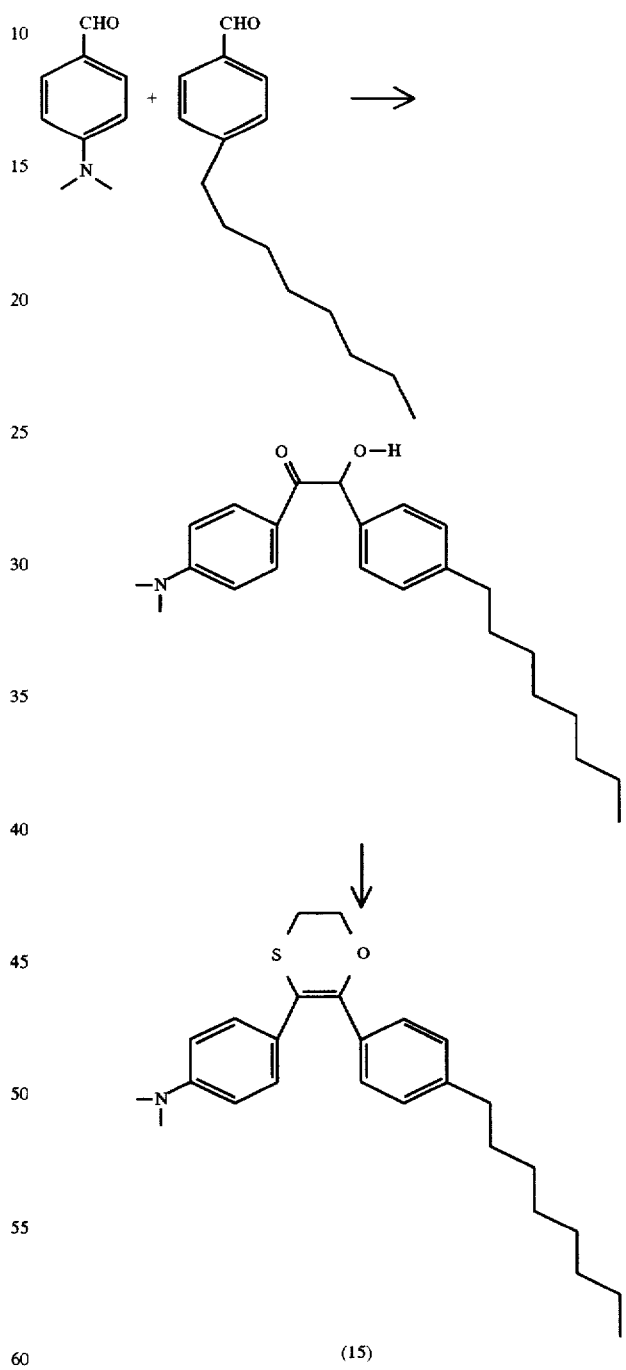

(15)

A. To a refluxing solution of 3.0 g of p-dimethylamino-benzaldehyde (20 mmole) and 2 g of potassium cyanide in 60% ethanol under argon was added 4.4 g of p-octyl benzaldehyde (20 mmole, Kodak) in 20 ml of ethanol in 90 minutes. The reaction mixture was refluxed for 15 minutes more and extracted with ethyl acetate (3×50 ml). The combined ethyl acetate solution was dried over sodium sulphate (50 g) and removed under reduced pressure. The product was purified on preparative TLC (hexane: ethyl acetate 5:1) to yield 1.2 g of substituted benzoin.

$^1$H NMR (CDCl$_3$, 250 MHz) : δ0.85 (t, 3H), 1.3 (m, 12H), 1.5 (m, 2H), 2.5 (t, 2H), 2.9 (s, 6H), 4.8 (d, 1H), 5.8 (d, 1H), 6.5 (d, 2H), 7.3 (q, 4H), 7.8 (d, 2H).

B. To a stirred solution of 0.94 g of substituted benzoin from Part A above (2.5 mmole) in 50 ml of dry toluene, 1.2 ml of 2-thioethanol (15 mmole) was added, followed by 2.5 ml of TMSCl. The reaction mixture was refluxed in an oil bath under argon for 30 hours. The reaction mixture was allowed to come to room temperature and poured into 150 ml of saturated bicarbonate solution. The organic layer was separated and washed with 100 ml of saturated bicarbonate solution. The combined aqueous layer was extracted with 75 nl of CH$_2$Cl$_2$. The combined organic solution was dried over sodium sulphate (50 g) and removed under reduced pressure. The product was purified on silica gel (CH$_2$Cl$_2$: ethyl acetate 9:1) to yield 0.75 g of C-8 thioxene Compound 15 as pale yellow solid. $^1$H NMR (CDCl$_3$, 250 MHz) : δ0.8 (t, 3H), 1.3 (m, 10H), 1.6 (m, 2H), 2.5 (t, 2H), 2.9 (s, 6H), 3.3 (t, 2H), 4.5 (t, 2H), 6.5 (d, 2H), 7.1 (d, 2H), 7.3 (m, 5H).

Mass Spectrum (CI: m/e, relative intensity) 409 (M$^+$100 ), 165 (40).

Absorption Spectra (Toluene) : 330 nm (ε3,000).

Example 5
Preparation of N-Phenyl Oxazine (Compound 16):

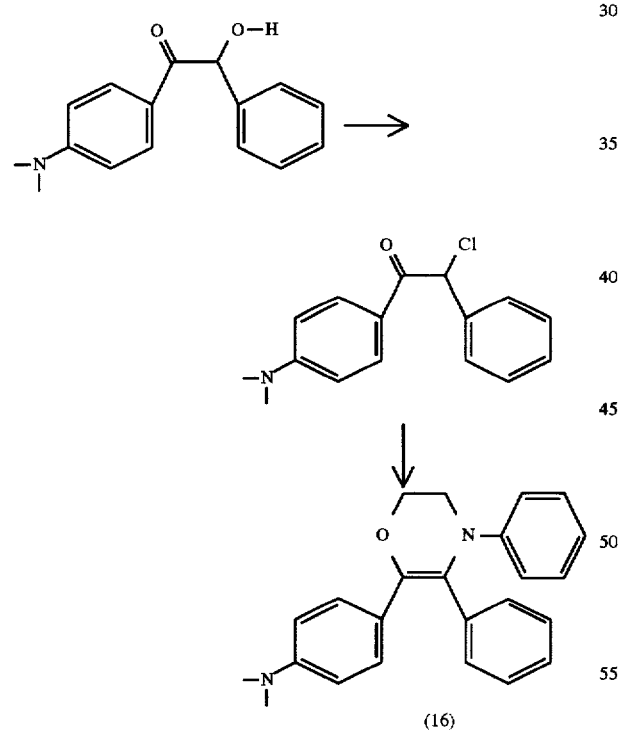

(16)

A. 5 g of p-dimethylaminobenzoin was dissolved in 5 ml of CH$_2$Cl$_2$ and stirred in an ice bath. 10 ml of SOCl$_2$ was added and the reaction mixture stirred for 1 hour. The solvent was removed under reduced pressure and the product was crystallized from MeOH. $^1$H NMR (CDCl$_3$, 250 MHz) : δ3.0 (s, 6H), 6.3 (s, 1H), 6.5 (d, 2H), 7.4 (m, 5H) 7.8 (d, 2H).

B. 0.271 g of P-(2-phenyl-2-chloro acetyl) dimethylamino-benzene (1 mmole) and 0.274 g of N-(2 hydroxy ethyl) aniline (2.0 mmole) were dissolved in 3 ml of dry ethanol and heated in a sealed tube at 80° C. for 8 hours. On cooling the product crystallized out as pale yellow needles, which was filtered and dried to yield 0.2 g of N-phenyl oxazine Compound 15.

1H NMR (CDCl$_3$, 250 MHz) δ3.0 (bs, 6H), 3.7 (bt, 2H), 4.4 (bt, 2H), 6.5 (bd, 2H), 7.4 (m, 12H).

Mass Spectrum (CI: m/e, relative intensity) 356 (M$^+$100), 180 (70).

Example 6
Preparation of N-Phenyl Indole Oxazine (Compound 17):

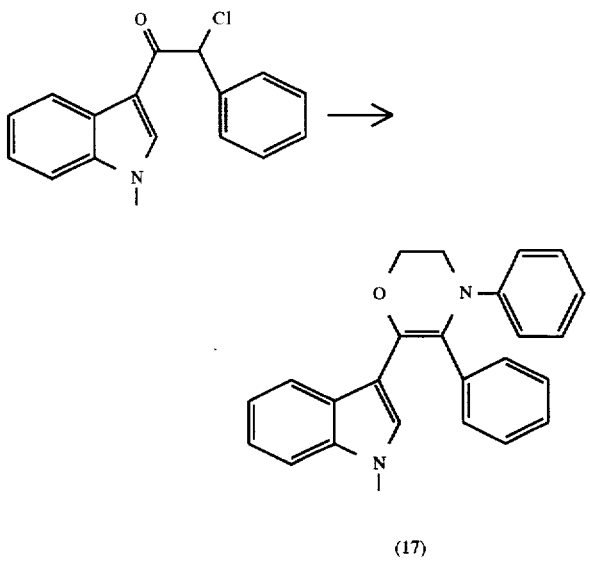

(17)

0.283 g of 3-(2-phenyl-2-chloro acetyl) N-methylindole (1 mmole) (H. Nakamura and T. Goto, Heterocyles, 10, 167–170 (1978), and 0.274 g of 2-anilino ethanol (2.0 mmole) were dissolved in 3 ml of dry ethanol and heated in a sealed tube at 80° C. for 8 hours. On cooling the product crystallized out as pale yellow needles which was filtered and dried to yield 0.21 g of N-phenyl indole oxazine Compound 17.

$^1$H NMR (CDCl$_3$, 250 MHz) : δ3.7 (bs, 3H), 3.8 (bt, 2H), 4.4 (bt, 2H), 7.2 (bm, 15H).

Mass Spectrum (CI: m/e, relative intensity) 366 (M$^+$100) 180 (70).

Example 7

Table 4 summarizes the properties of Compounds 11, 16, and 17 determined in a manner similar to that described in Example 2.

TABLE 4

Properties of Chemiluminescent Compounds And Compositions

| Compound** | λmax (AbS) | λmax (EMI) | λmax (CH.EM) | t½ | Φ |
|---|---|---|---|---|---|
| 11 | 330 nM | 400 nM | 400 nM | 2.1 sec | Low* (b) |
| 11 + Eu(TTA)$_3$ | | | 615 nM | 1.3 sec | 0.0024 (a) (b) |
| 11 + Eu(TTA)$_3$Phen | | | 615 nM | 1.8 sec | 0.14 (a) (b) |
| 16 | | 400 nM | 550 nM | 120 sec | Low* (b) |
| 16 + Eu(TTA)$_3$ | | | 615 nM | 11 sec | 0.005 |

TABLE 4-continued

Properties of Chemiluminescent Compounds And Compositions

| Compound** | λmax (AbS) | λmax (EMI) | λmax (CHEM) | t½ | Φ |
|---|---|---|---|---|---|
| (1.5 × 10⁻⁴ M) | | | | | |
| 16 + Eu(TTA)₃ | | | 615 nM | 3.5 sec | 0.04 |
| (5.0 × 10⁻⁴ M) | | | | | (b) (c) (d) |
| 17 | | | 550 nM | 120 sec | Low* |
| 17 + Eu(TTA)₃ | | | 615 nM | 12 sec | 0.04 |
| (0.6 × 10⁻⁴ M) | | | | | |
| 17 + Eu(TTA)₃ | | | 615 nM | 2 sec | 0.026 |
| (0.6 × 10⁻⁴ M) | | | | | (b) (c) (d) |

*less than 0.0003
**in toluene
a) $R^1O_2$— Rate of reaction of singlet oxygen with thioxene in toluene is $18.9 \times 10^7\ M^{-1}\ sec^{-1}$. After correction for regioisomers and rate of reaction, the quantum yield was determined.
b) Quantum yield determined by steady state method.
c) Assuming that the rate of reaction of singlet oxygen with morphilino oxene and dioxene is the same.
d) The rate of chemiluminescence decay and quantum yield depend on Eu(TTA)₃ concentration.

The above discussion includes certain theories as to mechanisms involved in the present invention. These theories should not be construed to limit the present invention in any way, since it has been demonstrated that the present invention achieves the results described.

The above description and examples disclose the invention including certain preferred embodiments thereof. Modifications of the methods described that are obvious to those of ordinary skill in the art are intended to be within the scope of the following claims and included within the metes and bounds of the invention.

What is claimed is:

1. A compound of the formula:

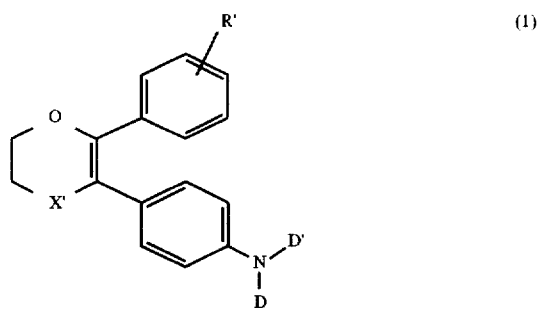

(1)

wherein X' is S and D and D' are $CH_3$ or $(CH_2)_9CH_3$ and R' is $(CH_2)_6CH_3$ or $(CH_2)_7CH_3$.

2. The compound of claim 1 wherein D and D' are $CH_3$ and R' is $(CH_2)_7CH_3$.

3. The compound of claim 1 wherein D and D' are $(CH_2)_9CH_3$ and R' is $(CH_2)_6CH_3$.

* * * * *